(12) United States Patent
Segi et al.

(10) Patent No.: US 9,814,371 B2
(45) Date of Patent: Nov. 14, 2017

(54) IMAGING MODULE, LENS-ATTACHED IMAGING MODULE, ENDOSCOPE, METHOD OF MANUFACTURING IMAGING MODULE, AND FLEXIBLE WIRING SUBSTRATE FORMATION APPARATUS

(71) Applicant: FUJIKURA LTD., Koto-ku, Tokyo (JP)

(72) Inventors: Takeshi Segi, Sakura (JP); Yusuke Matsuda, Sakura (JP); Katsuya Yamagami, Sakura (JP); Kenichi Nakatate, Sakura (JP)

(73) Assignee: FUJIKURA LTD., Koto-ku, Tokyo (JP)

( * ) Notice: Subject to any disclaimer, the term of this patent is extended or adjusted under 35 U.S.C. 154(b) by 262 days.

(21) Appl. No.: 14/020,160

(22) Filed: Sep. 6, 2013

(65) Prior Publication Data

US 2014/0009593 A1 Jan. 9, 2014

Related U.S. Application Data

(63) Continuation of application No. PCT/JP2013/059600, filed on Mar. 29, 2013.

(30) Foreign Application Priority Data

Mar. 30, 2012 (JP) ................. 2012-082972

(51) Int. Cl.
*A61B 1/04* (2006.01)
*H04N 9/47* (2006.01)
(Continued)

(52) U.S. Cl.
CPC ............ *A61B 1/005* (2013.01); *A61B 1/0011* (2013.01); *A61B 1/04* (2013.01); *A61B 1/051* (2013.01);
(Continued)

(58) Field of Classification Search
CPC ... A61B 1/051; A61B 1/0011; A61B 1/00096; A61B 1/005; A61B 2562/164; H04N 2005/2255
(Continued)

(56) References Cited

U.S. PATENT DOCUMENTS 5,220,198 A 6/1993 Tsuji
5,754,313 A 5/1998 Pelchy et al.
(Continued)

FOREIGN PATENT DOCUMENTS

JP 56-144673 A 11/1981
JP 04-218136 A 8/1992
(Continued)

OTHER PUBLICATIONS

Communication dated Mar. 26, 2015 from the European Patent Office in counterpart application No. 13753406.1.
(Continued)

*Primary Examiner* — Jared Walker
(74) *Attorney, Agent, or Firm* — Sughrue Mion, PLLC

(57) ABSTRACT

An imaging module of the invention includes: an electrical cable; a solid-state image sensing device; and a flexible wiring substrate including: a device-mounted portion onto which the solid-state image sensing device is mounted; two extended portions which bend at both sides of the device-mounted portion and extend from the device-mounted portion so as to come close to each other with increasing distance from the device-mounted portion; two connection end portions extending from the two extended portions along the direction of the axis of the front end of the electrical cable on an opposite side of the device-mounted portion; and terminals which are provided on the two connection end portions and connected to the electrical
(Continued)

cable, the flexible wiring substrate electrically connecting the solid-state image sensing device and the electrical cable.

14 Claims, 12 Drawing Sheets

(51) Int. Cl.
*A61B 1/005* (2006.01)
*G02B 23/24* (2006.01)
*A61B 1/00* (2006.01)
*H04N 5/225* (2006.01)
*A61B 1/05* (2006.01)
*H01L 23/00* (2006.01)

(52) U.S. Cl.
CPC ....... *G02B 23/2484* (2013.01); *H04N 5/2257* (2013.01); *H01L 24/11* (2013.01); *H01L 24/13* (2013.01); *H01L 24/16* (2013.01); *H01L 24/81* (2013.01); *H01L 2224/1134* (2013.01); *H01L 2224/1146* (2013.01); *H01L 2224/13101* (2013.01); *H01L 2224/16225* (2013.01); *H04N 2005/2255* (2013.01); *Y10T 29/49128* (2015.01); *Y10T 29/532* (2015.01)

(58) Field of Classification Search
USPC .......................................................... 348/76
See application file for complete search history.

(56) References Cited

U.S. PATENT DOCUMENTS

| | | | |
|---|---|---|---|
| 6,150,716 A | 11/2000 | MacQuarrie et al. | |
| 6,635,865 B1 | 10/2003 | Soltyk | |
| 2002/0080233 A1 | 6/2002 | Irion et al. | |
| 2004/0167378 A1 | 8/2004 | Ando | |
| 2005/0133245 A1* | 6/2005 | Katsuyama | H01R 9/031 174/74 R |
| 2008/0111907 A1 | 5/2008 | Ito et al. | |
| 2011/0063428 A1 | 3/2011 | Sonnenschein et al. | |
| 2011/0245600 A1* | 10/2011 | Ishii | A61B 1/05 600/104 |
| 2011/0245608 A1* | 10/2011 | Takahashi | A61B 1/00096 600/109 |
| 2011/0249106 A1* | 10/2011 | Makino | H04N 5/2254 348/76 |
| 2011/0279675 A1 | 11/2011 | Mano et al. | |
| 2011/0295064 A1* | 12/2011 | Kagawa | A61B 1/051 600/110 |
| 2012/0071870 A1* | 3/2012 | Salahieh | A61B 5/01 606/33 |

FOREIGN PATENT DOCUMENTS

| | | |
|---|---|---|
| JP | 04-218316 A | 8/1992 |
| JP | 2008-118568 A | 5/2008 |
| JP | 2008-227733 A | 9/2008 |
| JP | 2009-260553 A | 11/2009 |
| JP | 2010-258582 A | 11/2010 |
| JP | 2011-217887 A | 11/2011 |
| RU | 2191445 C2 | 10/2002 |
| WO | 00/72744 A2 | 12/2000 |
| WO | 2011/111248 A1 | 9/2015 |

OTHER PUBLICATIONS

Machine translation for JP 2008-118568 filed Jan. 23, 2014.
International Search Report for PCT/JP2013/059600, dated Apr. 23, 2013.
European Search Report issued in European Application No. 13753406.1 mailed Dec. 3, 2014.
Office Action issued by Japanese Patent Office in Japanese Application No. 2012-082972 mailed Jan. 27, 2015.
Machine Translation of JP 2010-258582, which was filed in an IDS on Sep. 6, 2013.
Communication dated Sep. 7, 2015 from the Russian Patent Office in counterpart application No. 2013143312/07.
Communication dated Mar. 1, 2016, from the Japanese Patent Office in counterpart application No. 2012-082972.
Communication dated Feb. 4, 2016, from the State Intellectual Property Office of the People's Republic of China in counterpart application No. 201380000931.5.
Communication dated Jan. 24, 2017, from the Japanese Patent Office in counterpart Japanese application No. 2016-073676.
Communication dated Jan. 24, 2017 from the Japanese Patent Office in counterpart Japanese application No. 2016-073677.
Communication dated Apr. 6, 2017, from the European Patent Office in counterpart European Application No. 13753406.1.

* cited by examiner

FIG. 3A PART A
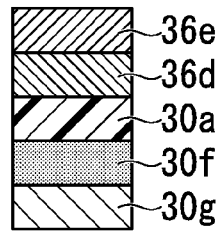
FIG. 3B PART B
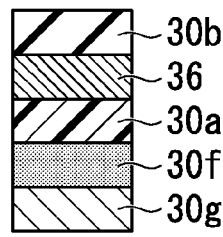
FIG. 3C PART C
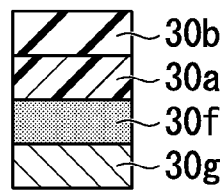
FIG. 3D PART D
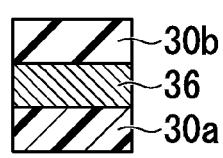
FIG. 3E PART E

53a 53A (53)

53a 53B (53)

53a 53C (53)

IMAGING MODULE, LENS-ATTACHED IMAGING MODULE, ENDOSCOPE, METHOD OF MANUFACTURING IMAGING MODULE, AND FLEXIBLE WIRING SUBSTRATE FORMATION APPARATUS

CROSS REFERENCE TO RELATED APPLICATIONS

This application is a continuation application based on a PCT Patent Application No. PCT/JP2013/059600, filed Mar. 29, 2013, whose priority is claimed on Japanese Patent Application No. 2012-082972 filed on Mar. 30, 2012, the content of which is hereby incorporated by reference.

BACKGROUND OF THE INVENTION

The present invention relates to an imaging module having a structure in which a solid-state image sensing device is electrically connected to an electrical cable via a flexible wiring substrate, a lens-attached imaging module configured to use the imaging module, an endoscope, a method of manufacturing an imaging module, and a flexible wiring substrate formation apparatus.

DESCRIPTION OF THE RELATED ART

As a conventional electronic endoscope, a structure have been often adopted which accommodates an imaging module in which an imaging unit including a solid-state image sensing device (hereinafter, simply referred as to imaging device) is fitted to a front end of an electrical cable in an insertion portion of an electronic endoscope.

As such an imaging unit of the imaging module, a structure have been widely adopted which accommodates a flexible wiring substrate (hereinafter, referred to as FPC), onto which the imaging device is mounted, and a field lens unit in a tubular metal frame member, and electrically connects the imaging device to the electrical cable via the FPC (for example, Japanese Unexamined Patent Application, First Publication No. 2009-260553 and Japanese Unexamined Patent Application, First Publication No. 2008-227733).

The FPC is attached to an electrical cable so that terminals are soldered to conductors, and has a cable-connection end portion disposed roughly along the axis line of a metal frame member.

The imaging device is formed at the FPC so as to be perpendicular to the axis line of a metal frame member by folding the FPC and is mounted on a device-mounted portion located at the front side of the cable-connection end portion (on the opposite side of the electrical cable).

In order to realize excellent imaging by using such an imaging unit, it is necessary to dispose the imaging device in a suitable direction relative to the optical axis of a field lens unit fixed inside the front-end portion of a metal tubular member.

However, the aforementioned Japanese Unexamined Patent Application, First Publication No. 2009-260553 and Japanese Unexamined Patent Application, First Publication No. 2008-227733 disclose a structure in which an imaging device is mounted on a pendent device-mounted portion in a form of cantilever by folding the FPC, since the configuration of the front edge of the FPC (near device-mounted portion, the position close to the device-mounted portion) is unstable, it is difficult to stabilize the device-mounted portion and the imaging device in a proper direction relative to the optical axis of a field lens unit.

Moreover, as an imaging unit, a structure in which a block is adhesively-fixed to the inside of a U-shaped bent FPC has been also proposed as disclosed in Japanese Unexamined Patent Application, First Publication No. 2011-217887.

With this configuration, the shape of the front edge of the FPC can be stably maintained.

However, in the case of this configuration, since a high-precision-machined block is required and it is also necessary to fix the FPC relative to the block with precision, assembly thereof has been complicated.

Furthermore, in the case of using a structure in which conductors of an electrical cable are soldered on portions disposed at both sides via the block of the FPC, the size thereof, including coatings covering the soldered portions or the conductors, cannot be easily reduced, there were disadvantages in terms of downsizing of the imaging unit (reduction in the diameter of the imaging unit) and downsizing of a tube of an endoscope (reduction in the diameter of the endoscope).

In recent years, for example, as disclosed in United States Patent Application, Publication No. 2011/0063428 (for example, claim 1), an imaging unit having an external diameter of approximately 1.1 mm (camcorder head of Japanese Unexamined Patent Application, First Publication No. 2009-260553) has been proposed.

In the case of using such an imaging unit having the foregoing external diameter, the thickness of an electrical cable to be soldered on the FPC or the size of soldered portions significantly influence the external diameter of the entire imaging unit.

SUMMARY OF THE INVENTION

The present invention was conceived in view of the above-described problems and has an object thereof to provide an imaging module, a lens-attached imaging module, an endoscope, a method of manufacturing an imaging module, and a flexible wiring substrate formation apparatus, which can easily realize and maintain stability of the configuration close to a device-mounted portion and a device-mounted portion of a flexible wiring substrate, can efficiently manufacture them at a low cost, and can easily reduce the diameter thereof.

In order to solve the aforementioned problems, the invention provides the following constitutions.

An imaging module of a first aspect of the invention includes: an electrical cable; a solid-state image sensing device including an imaging unit orthogonal to a direction of an axis of a front end of the electrical cable; and a flexible wiring substrate including: a device-mounted portion onto which the solid-state image sensing device is mounted; two extended portions which bend at both sides of the device-mounted portion and extend from the device-mounted portion so as to come close to each other with increasing distance from the device-mounted portion; two connection end portions extending from the two extended portions along the direction of the axis of the front end of the electrical cable on an opposite side of the device-mounted portion; and terminals which are provided on the two connection end portions and connected to the electrical cable, the flexible wiring substrate electrically connecting the solid-state image sensing device to the electrical cable.

In the imaging module of the first aspect of the invention, it is preferable that the device-mounted portion, the extended portions, and the connection end portions be provided only on one face of the flexible wiring substrate.

In the imaging module of the first aspect of the invention, it is preferable that the solid-state image sensing device include: a top face on which the imaging unit is provided; a back face electrically connected to the device-mounted portion of the flexible wiring substrate; and wiring formed on the top face; and wiring formed on the back face, and the wirings formed on the top face and on the back face be electrically connected through a through-hole interconnection which is formed and penetrated though the solid-state image sensing device.

In the imaging module of the first aspect of the invention, it is preferable that a width of each of the two extended portions be smaller than a width of the connection end portions extending from the extended portions.

In the imaging module of the first aspect of the invention, it is preferable that the flexible wiring substrate be located at both sides of the device-mounted portion of the flexible wiring substrate and include a bend portion protruding from a projection range of the solid-state image sensing device in the device-mounted portion.

In the imaging module of the first aspect of the invention, it is preferable that an insulation protection material do not coat the bend portion of the flexible wiring substrate so that wiring is exposed.

In the imaging module of the first aspect of the invention, it is preferable that a cut-off portion be formed at the bend portion of the flexible wiring substrate.

It is preferable that the imaging module of the first aspect of the invention further include an insulating tube collectively accommodating the two connection end portions of the flexible wiring substrate and covering at least part of a connection portion between the flexible wiring substrate and the electrical cable.

It is preferable that the imaging module of the first aspect of the invention further include an insulating tube externally fitted onto each of the two connection end portions of the flexible wiring substrate, covering at least part of a connection portion between the flexible wiring substrate and the electrical cable.

In the imaging module of the first aspect of the invention, it is preferable that the insulating tube be configured to include a half-divided structure in which a pair of tube divided bodies are connected to and integrated with each other.

In the imaging module of the first aspect of the invention, it is preferable that at least part of an internal space formed by the device-mounted portion and the two extended portions be filled with resin and at least a part of the two extended portions be thereby fixed.

In the imaging module of the first aspect of the invention, it is preferable that the two connection end portions be fixed to each other, and the flexible wiring substrate have a flexible portion located between a portion at which the two extended portions are fixed and a portion at which the two connection end portions are fixed.

A lens-attached imaging module of a second aspect of the invention includes: a flexible wiring substrate and a solid-state image sensing device which constitute the imaging module of the above-mentioned first aspect; a lens unit fixed to the solid-state image sensing device; and a sleeve-shaped metal frame member accommodating the flexible wiring substrate, the solid-state image sensing device, and the lens unit.

An endoscope of a third aspect of the invention includes: an insertion portion; and the lens-attached imaging module of the aforementioned second aspect, housed in the insertion portion.

A method of manufacturing an imaging module of a fourth aspect of the invention includes: preparing an elongated flexible wiring substrate having a device-mounted portion located at a center region in a longitudinal direction thereof; mounting a solid-state image sensing device onto a mount face of the device-mounted portion (device mounting step); bending portions which are located at both sides of the device-mounted portion, from the device-mounted portion, thereby forming two extended portions extending from the device-mounted portion to a back face side opposite to the mount face of the device-mounted portion and two connection end portions, the two connection end portions extending from the two extended portions, respectively (bending-shaping step); filling an inside region surrounded by the two extended portions and the device-mounted portion (which is formed in the bending-shaping step) with resin, and adhesively fixing the two extended portions to each other (adhesively-fixing step); and connecting an electrical cable to a terminal provided at an external face side of each of the two connection end portions (which is formed in the bending-shaping step) (cable connecting step).

A method of manufacturing an imaging module of a fifth aspect of the invention includes: preparing an elongated flexible wiring substrate having a device-mounted portion located at a center region in a longitudinal direction thereof; mounting a solid-state image sensing device onto a mount face of the device-mounted portion (device mounting step); connecting an electrical cable to a terminal provided at an external face side of each of two connection end portions of the flexible wiring substrate (cable connecting step); bending portions which are located at both sides of the device-mounted portion, from the device-mounted portion, thereby forming two extended portions extending from the device-mounted portion to a back face side opposite to the mount face of the device-mounted portion and the two connection end portions, the two connection end portions extending from the two extended portions, respectively (bending-shaping step); and filling an inside region surrounded by the two extended portions and the device-mounted portion (which is formed in the bending-shaping step) with resin, and adhesively fixing the two extended portions to each other (adhesively-fixing step).

In the method of manufacturing an imaging module of the fourth aspect and the fifth aspect of the invention, after the inside region surrounded by the two extended portions and the device-mounted portion is filled with the resin, the two extended portions may be adhesively fixed to each other.

In the method of manufacturing an imaging module of the fourth aspect and the fifth aspect of the invention, before the inside region surrounded by the two extended portions and the device-mounted portion is filled with the resin, the two extended portions may be adhesively fixed to each other.

A flexible wiring substrate formation apparatus of a sixth aspect of the invention includes: a flexible-wiring-substrate mounting stage on which an elongated flexible wiring substrate is to be mounted; a pin-attached elevating stage including: an elevating stage capable of moving up and down relative to the flexible-wiring-substrate mounting stage; a pin protruding from the elevating stage; and a flat mounted-portion contacting face with which a device-mounted portion comes into contact, the device-mounted portion being located at a center region of the flexible wiring substrate in a longitudinal direction thereof, the mounted-portion contacting face being formed around the pin; and a pair of movable pressing members provided on the flexible-wiring-substrate mounting stage, varying a separated distance therebetween by sliding motion along an upper surface of the flexible-wiring-substrate mounting stage, wherein the pin-attached elevating stage is movable between an initial position and a safety position due to elevation of the pin-attached elevating stage, an upper face of the pin-attached elevating stage substantially coincides with the upper surface of the flexible-wiring-substrate mounting stage at the initial position, the safety position is located under the initial position.

A method of manufacturing an imaging module of a seventh aspect of the invention includes: preparing an elongated flexible wiring substrate having a device-mounted portion located at a center region in a longitudinal direction thereof; mounting a solid-state image sensing device onto a mount face of the device-mounted portion (device mounting step); using a flexible wiring substrate formation apparatus, the flexible wiring substrate formation apparatus including: a flexible-wiring-substrate mounting stage on which the flexible wiring substrate is to be mounted; a pin-attached elevating stage including: an elevating stage capable of moving up and down relative to the flexible-wiring-substrate mounting stage; a pin protruding from the elevating stage; and a flat mounted-portion contacting face with which a device-mounted portion comes into contact, the device-mounted portion being located at a center region of the flexible wiring substrate in a longitudinal direction thereof, the mounted-portion contacting face being formed around the pin; and a pair of movable pressing members provided on the flexible-wiring-substrate mounting stage, varying a separated distance therebetween by sliding motion along an upper surface of the flexible-wiring-substrate mounting stage, the pin-attached elevating stage being movable between an initial position and a safety position due to elevation of the pin-attached elevating stage, an upper face of the pin-attached elevating stage substantially coinciding with the upper surface of the flexible-wiring-substrate mounting stage at the initial position, the safety position being located under the initial position; allowing the device-mounted portion of the flexible wiring substrate to come into contact with the mounted-portion contacting face provided at the pin of the pin-attached elevating stage positioned at the initial position, bending portions which are located at both sides of the device-mounted portion of the flexible wiring substrate, from the device-mounted portion, placing rear portions at a gap between the pair of movable pressing members in an opened state, the rear portions extending from the device-mounted portion to a rear side opposite to the mount face of the device-mounted portion (flexible wiring substrate mounting step); allowing the pair of movable pressing members to approach each other, and allowing a pair of the rear portions of the flexible wiring substrate to approach each other, thereby forming two extended portions and two connection end portions, the two connection end portions extending from the two extended portions, respectively (bending-shaping step); moving the pin-attached elevating stage downwardly from the initial position to the safety position, detaching the pin from a space surrounded by the device-mounted portion and the extended portions located at both sides of the device-mounted portion, filling the space with resin, and curing the resin (adhesively-fixing step); and connecting an electrical cable to a terminal provided at an external face side of each of the two connection end portions (which is formed in the bending-shaping step) (cable connecting step).

A method of manufacturing an imaging module of an eighth aspect of the invention includes: preparing an elongated flexible wiring substrate having a device-mounted portion located at a center region in a longitudinal direction thereof; mounting a solid-state image sensing device onto a mount face of the device-mounted portion (device mounting step); connecting an electrical cable to a terminal provided at an external face side of each of two connection end portions of the flexible wiring substrate (cable connecting step); using a flexible wiring substrate formation apparatus, the flexible wiring substrate formation apparatus including: a flexible-wiring-substrate mounting stage on which the flexible wiring substrate is to be mounted; a pin-attached elevating stage including: an elevating stage capable of moving up and down relative to the flexible-wiring-substrate mounting stage; a pin protruding from the elevating stage; and a flat mounted-portion contacting face with which a device-mounted portion comes into contact, the device-mounted portion being located at a center region of the flexible wiring substrate in a longitudinal direction thereof, the mounted-portion contacting face being formed around the pin; and a pair of movable pressing members provided on the flexible-wiring-substrate mounting stage, varying a separated distance therebetween by sliding motion along an upper surface of the flexible-wiring-substrate mounting stage, the pin-attached elevating stage being movable between an initial position and a safety position due to elevation of the pin-attached elevating stage, an upper face of the pin-attached elevating stage substantially coinciding with the upper surface of the flexible-wiring-substrate mounting stage at the initial position, the safety position being located under the initial position; allowing the device-mounted portion of the flexible wiring substrate to come into contact with the mounted-portion contacting face provided at the pin of the pin-attached elevating stage positioned at the initial position, bending portions which are located at both sides of the device-mounted portion of the flexible wiring substrate, from the device-mounted portion, placing rear portions at a gap between the pair of movable pressing members in an opened state, the rear portions extending from the device-mounted portion to a rear side opposite to the mount face of the device-mounted portion (flexible wiring substrate mounting step); allowing the pair of movable pressing members to approach each other, and allowing a pair of the rear portions of the flexible wiring substrate to approach each other, thereby forming two extended portions and the two connection end portions, the two connection end portions extending from the two extended portions, respectively (bending-shaping step); and moving the pin-attached elevating stage downwardly from the initial position to the safety position, detaching the pin from a space surrounded by the device-mounted portion and the extended portions located at both sides of the device-mounted portion, filling the space with resin, and curing the resin (adhesively-fixing step).

In the method of manufacturing an imaging module of the seventh aspect and the eighth aspect of the invention, after the space is filled with the resin, the two extended portions may be adhesively fixed to each other.

In the method of manufacturing an imaging module of the seventh aspect and the eighth aspect of the invention, before the space is filled with the resin, the two extended portions may be adhesively fixed to each other.

Effects of the Invention

According to the invention, by adopting the structure including two extended portions which bend at both sides of the device-mounted portion and which extend so as to approach each other with increasing distance from the device-mounted portion, the flexible wiring substrate can easily ensure the shape stability near the device-mounted portion (the position close to the device-mounted portion).

Accordingly, when the imaging module is assembled by accommodating the flexible wiring substrate having the solid-state image sensing device mounted on the device-mounted portion in the metal frame member, it is possible to easily adjust the direction and the position of the solid-state image sensing device or the device-mounted portion in the metal frame member with a high level of accuracy.

In addition, the imaging module related to the invention does not need a member such as a block or the like disclosed in Japanese Unexamined Patent Application, First Publication No. 2011-217887 to which a flexible wiring substrate is attached and which maintains the configuration thereof, and can be efficiently manufactured at a low cost.

Furthermore, according to the invention, the constitution in which the electrical cable is connected to the connection end portions which extend from two extended portions, respectively, is adopted.

According the this configuration, the distance between both connection end portions is made smaller than the distance between the extended portions, and the size thereof, including the cable connection portion at which the electrical cable is connected to the connection end portions, can be thereby easily reduced; and in the case of accommodating the solid-state image sensing device of the imaging module and the flexible wiring substrate in the metal frame member, the diameter of this metal frame member can be simply reduced.

BRIEF DESCRIPTION OF THE DRAWINGS

FIG. 3A is a view showing a cross-section structure of part A of the flexible wiring substrate shown in FIG. 2.

FIG. 3B is a view showing a cross-section structure of part B of the flexible wiring substrate shown in FIG. 2.

FIG. 3C is a view showing a cross-section structure of part C of the flexible wiring substrate shown in FIG. 2.

FIG. 3D is a view showing a cross-section structure of part D of the flexible wiring substrate shown in FIG. 2.

FIG. 3E is a view showing a cross-section structure of part E of the flexible wiring substrate shown in FIG. 2.

DETAILED DESCRIPTION OF THE INVENTION

Hereinafter, an embodiment of the invention will be described with reference to drawings.

Figure 1:
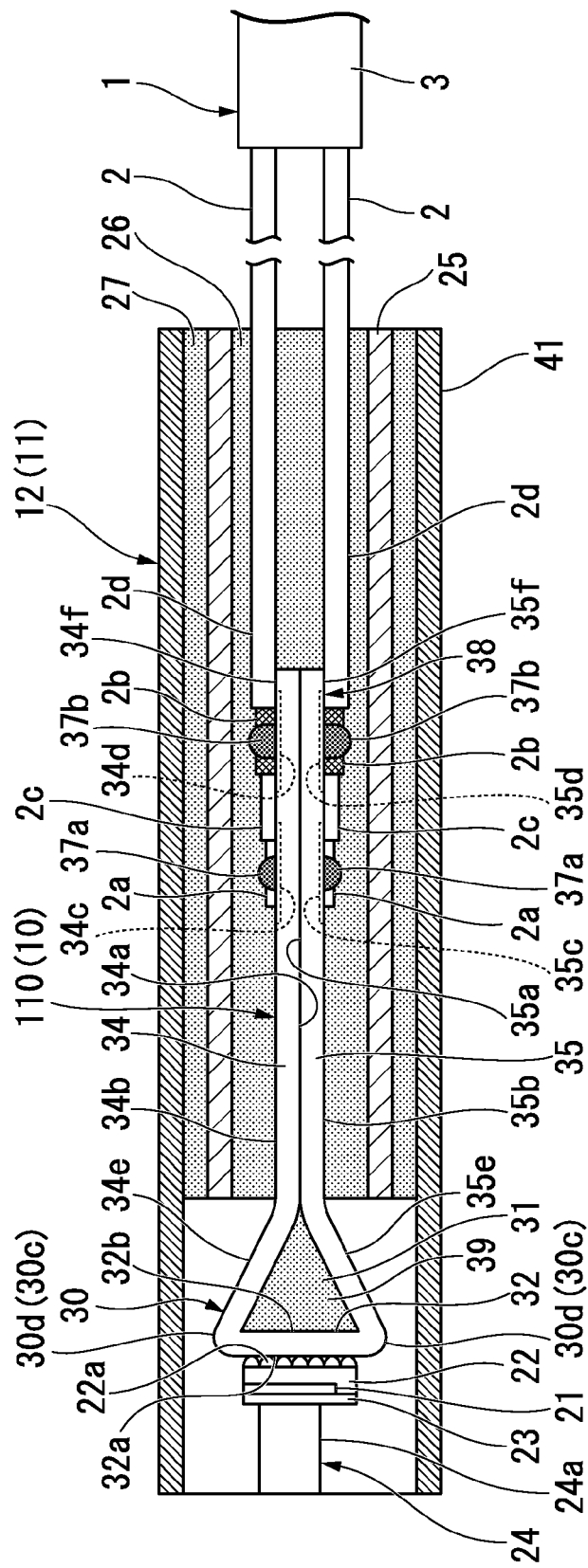
FIG. 1 is a cross-sectional view showing an imaging module of an embodiment related to the invention and a structure of a front-end imaging unit of a lens-attached imaging module configured by use of the imaging module.

FIG. 1 shows an imaging module 10 and a front end structure (front edge) of a lens-attached imaging module 11 assembled by use of the imaging module 10 of an embodiment related to the invention.

Figure 5A:
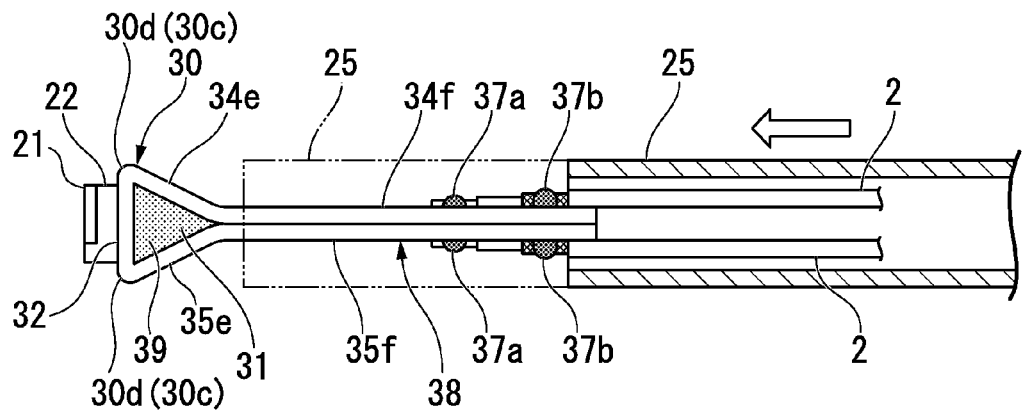
FIG. 5A is a view illustrating part of a step of assembling the imaging module shown in FIG. 1 and showing a step of externally fitting an insulating tube onto an extended tail portion of the flexible wiring substrate from the rear side of the extended tail portion.
Figure 5B:
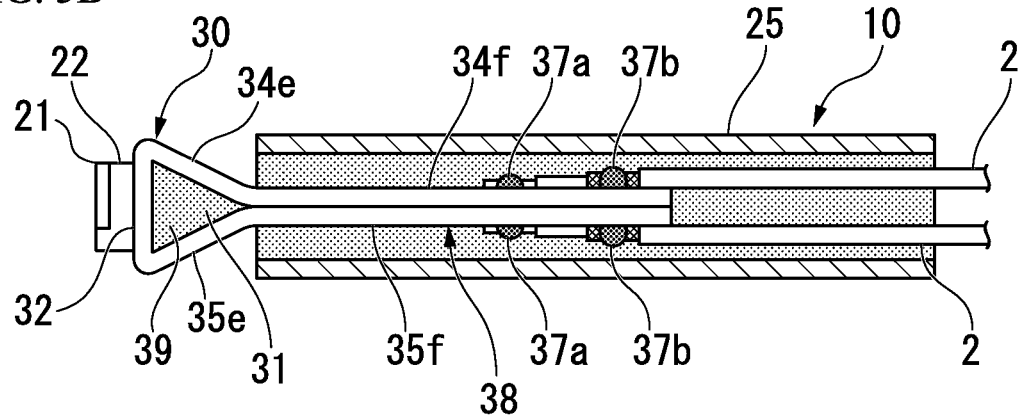
FIG. 5B is a view illustrating part of a step of assembling the imaging module shown in FIG. 1 and showing steps of accommodating the extended tail portion in the insulating tube in the step shown in FIG. 5A, filling the inside of the insulating tube with resin, and adhesively-integrating the insulating tube into the flexible wiring substrate by curing the resin.

As shown in FIGS. 1 and 5B, in the imaging module 10, a flexible wiring substrate 30 (flexible printed board), onto which a solid-state image sensing device 22 (hereinafter, simply referred to as imaging device) including an imaging unit 21 is mounted, is electrically connected and attached to a front end of a conductor of an electrical cable 1 (internal conductor 2a and external conductor 2b which will be described later).

As the imaging device 22, for example, a CMOS (complementary metal oxide semiconductor) can be preferably used.

The imaging module 10 includes a front-edge unit 110 in which the imaging device 22 is mounted on the flexible wiring substrate 30.

The imaging module 10 is configured so that the imaging device 22 is electrically connected to the electrical cable 1 through the flexible wiring substrate 30.

As shown in FIG. 5B, the flexible wiring substrate 30 includes a device-mounted portion 32 having a mount face 32a located at a front side and two rear portions 34 and 35.

The imaging device 22 is mounted on the mount face 32a.

The rear portions 34 and 35 are portions which bend at both sides of the device-mounted portion 32 and extend from the device-mounted portion 32 to a back side of the device-mounted portion 32.

Moreover, hereinbelow, one of the two rear portions 34 and 35 is referred to as a first rear portion 34 and the other thereof is referred to as a second rear portion 35.

Figure 2:
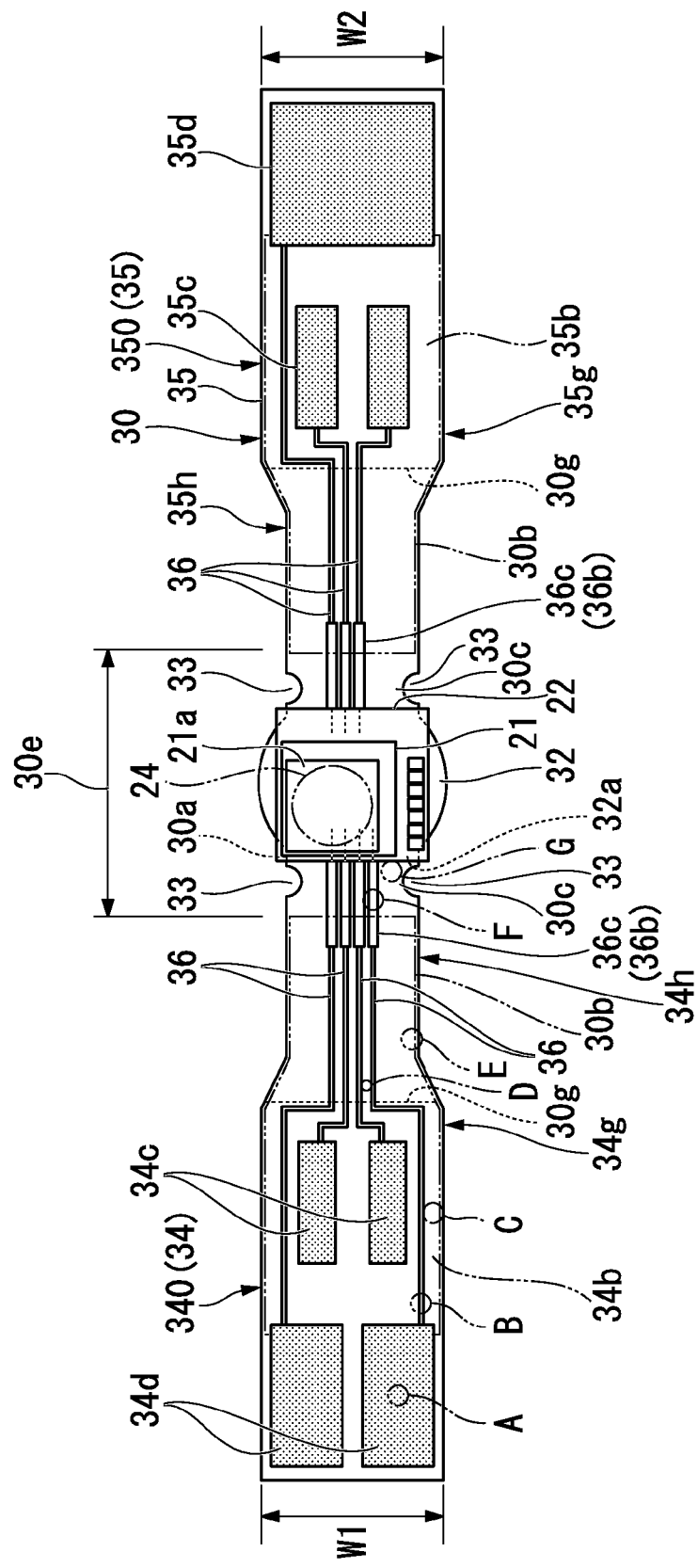
FIG. 2 is a view showing an example of a flexible wiring substrate used for the imaging module shown in FIG. 1 and is a plan view illustrating a state before bending the substrate (before folding).

In the flexible wiring substrate 30, the two rear portions 34 and 35 extending from both sides of the device-mounted portion 32 to the back side of the device-mounted portion 32 are formed by folding, at both sides of the device-mounted portion 32, an elongated substrate having the device-mounted portion 32 located at a center region in longitudinal direction as shown in FIG. 2.

Additionally, the flexible wiring substrate 30 is a one-side-wiring type flexible wiring substrate (wiring is formed only on one of the surfaces of the substrate (only one surface (outer surface))).

The wiring is provided on external surface side of the folded flexible wiring substrate 30.

Outer surfaces 34b and 35b (external face) are formed on a side opposite to opposed faces 34a and 35a of the two rear portions 34 and 35, respectively.

Pad-shaped terminals 34c and 34d are provided on the outer surface 34b. Similarly, pad-shaped terminals 35c and 35d are provided on the outer surface 35b (external face).

Built-in electrical cables 2, which are opened at the front end of the electrical cable 1, are electrically connected to terminals of the rear portions 34 and 35 located at both sides of the flexible wiring substrate 30, and the flexible wiring substrate 30 is thereby provided at the front end of the electrical cable 1.

Figure 13:
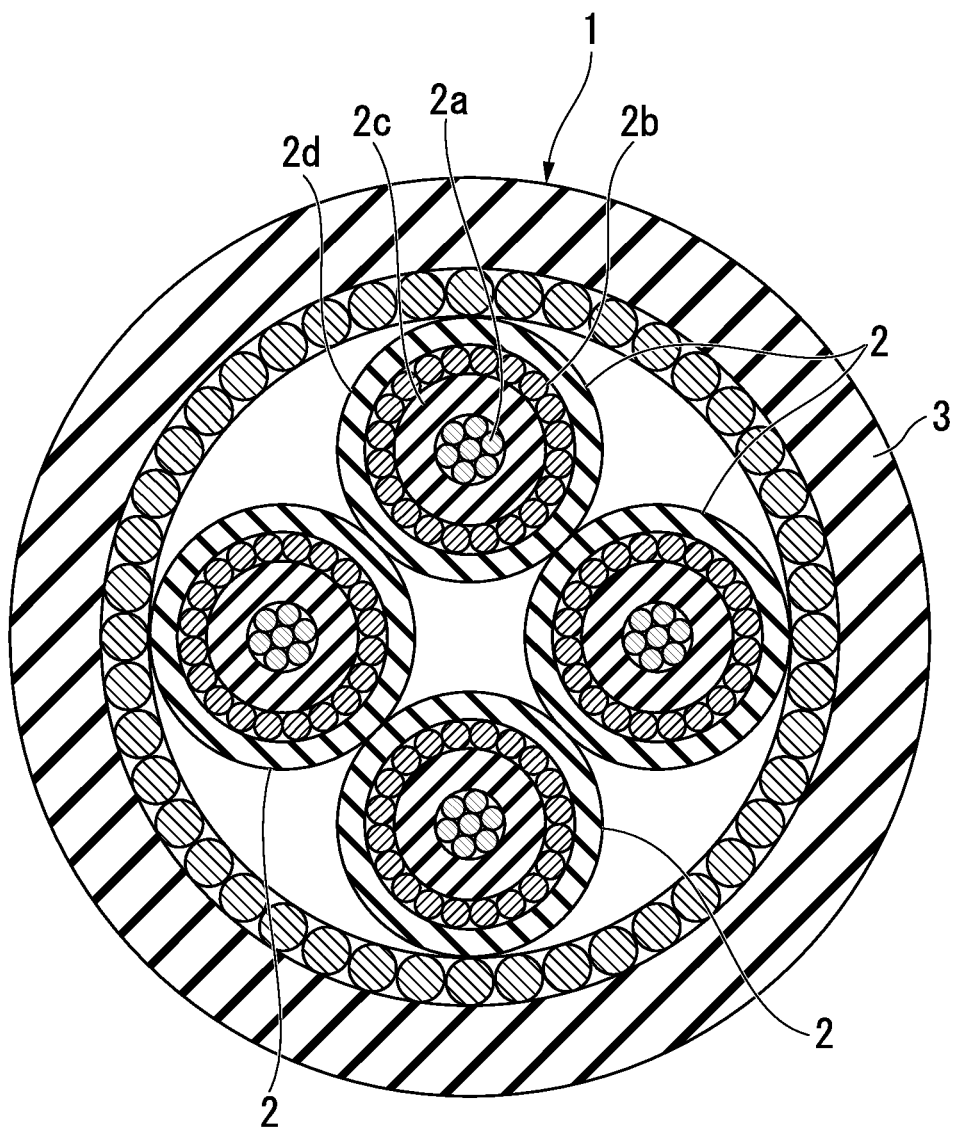
FIG. 13 is a view showing an example of a cross-section structure of an electrical cable of the imaging module shown in FIG. 1.

As shown in FIGS. 1 and 13, the built-in electrical cable 2 is a coaxial cable (electrical cable).

The electrical cable 1 is a cable unit in which a plurality of built-in electrical cables 2 (four shown as an example) are integrally coated with an outer coating 3.

The built-in electrical cables 2 include: the internal conductor 2a; a first coating layer 2c coating the internal conductor 2a; the external conductor 2b which is formed to be netted by metal thin wires and provided around the first coating layer 2c; and a second coating layer 2d coating the external conductor 2b.

As shown in FIGS. 1 and 2, an internal conductor terminal 34c to be electrically connected to the internal conductor 2a exposed at the front end of the built-in electrical cable 2 and an external conductor terminal 34d to be electrically connected to the external conductor 2b of the built-in electrical cable 2 are provided on the outer surface 34b of the rear portion 34 (surface on a side opposite to the opposed face 34a).

Similarly, an internal conductor terminal 35c to be electrically connected to the internal conductor 2a exposed at the front end of the built-in electrical cable 2 and an external conductor terminal 35d to be electrically connected to the external conductor 2b of the built-in electrical cable 2 are provided on the outer surface 35b of the rear portion 35 (surface on a side opposite to the opposed face 35a).

Two internal conductor terminals 34c and two external conductor terminals 35d are provided on the first rear portion 34.

Consequently, the internal conductor 2a is solder-mounted on the internal conductor terminals 34c, and two built-in electrical cables 2 having the external conductor 2b, which is solder-mounted on the external conductor terminals 34d, are connected to the first rear portion 34.

On the other hand, two internal conductor terminals 35c and single external conductor terminal 35d having the size dramatically larger than that of the internal conductor terminal 35c are provided on the second rear portion 35.

Consequently, the internal conductor 2a is solder-mounted on the internal conductor terminals 35c, and two built-in electrical cables 2 having the external conductor 2b, which is solder-mounted on the external conductor terminals 35d, are connected to the second rear portion 35.

As shown in FIGS. 1 and 2, the imaging unit 21 is electrically connected to wirings 36 of the flexible wiring substrate 30 through an electrical circuit formed on the imaging device 22 (refer to FIG. 2).

The imaging device 22 includes solder bumps, stud bumps, or plated bumps 22a (hereinafter, referred to as bump 22a) electrically connected to the electrical circuit of the imaging device 22 on the back face on the opposite side of the surface on which the imaging unit 21 is mounted (refer to FIG. 1).

The bumps 22a are securely connected to terminals 36a (refer to FIG. 14, hereinafter, referred to as terminal of mount portion) formed on the mount face 32a of the device-mounted portion 32 of the flexible wiring substrate 30 by use of a flip-chip method, the bumps are electrically connected to the wirings 36, and the imaging device 22 is thereby mounted on the device-mounted portion 32 of the flexible wiring substrate 30.

Figure 14:
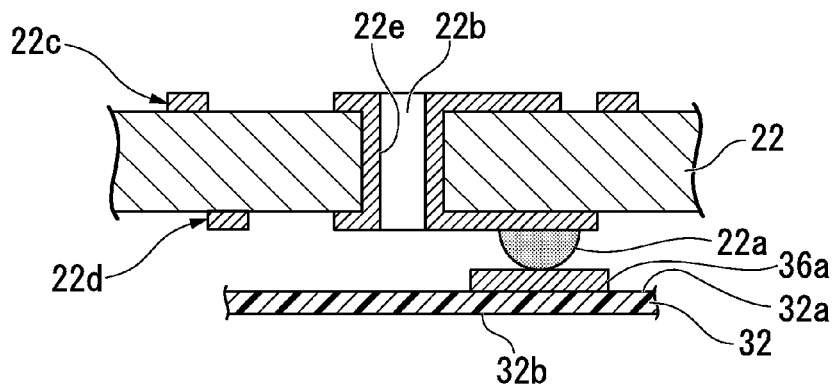
FIG. 14 is an enlarged cross-sectional view showing a structure adjacent to a device-mounted portion (position close to the device-mounted portion) of a flexible wiring substrate of the imaging module shown in FIG. 1.

In other cases, as shown in FIG. 14, the electrical circuit of the imaging device 22 may include, for example, a through-hole interconnection 22e (through-hole wiring) which is formed in a through hole 22b penetrating through a board of the imaging device 22 and is electrically connected to wirings 22c and 22d formed on both upper and lower faces of the imaging device 22.

As shown in FIG. 2, the terminals 36a of the mount portion of the flexible wiring substrate 30 are electrically connected to each of the terminals 34c, 34d, 35c, and 35d formed integrally with the wiring 36 through the wiring 36 of the flexible wiring substrate 30, respectively.

Accordingly, in the imaging module 10 shown in FIGS. 1, 5A, or the like as an example, the imaging unit 21 is electrically connected to the internal conductor 2a and the external conductor 2b of the built-in electrical cable 2 via the electrical circuit of the imaging device 22 and the wiring 36 of the flexible wiring substrate 30.

Figure 6:
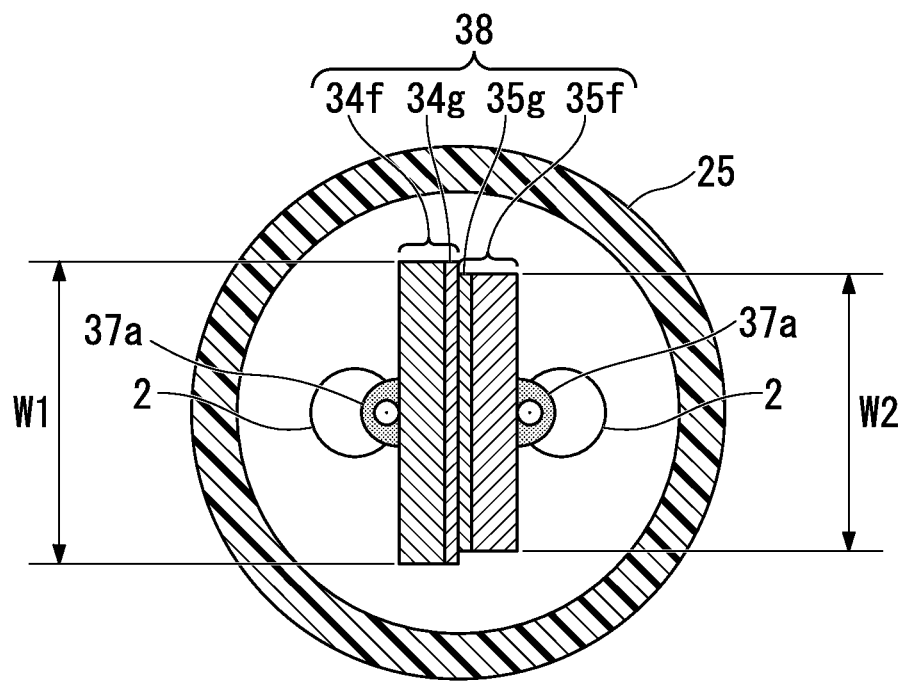
FIG. 6 is a cross-sectional view showing a state where the insulating tube is externally fitted onto the extended tail portion of the flexible wiring substrate.

As shown in FIGS. 5B and 6, the imaging module 10 includes an electrical insulation tube 25 (insulating tube).

The tube 25 accommodates and covers the two rear portions 34 and 35 and the front end of the built-in electrical cables 2 which are electrically connected to the terminals of the rear portions 34 and 35 by solder-mounting the internal conductor 2a and the external conductor 2b thereonto, respectively. The insulating tube 25 is a resin tube made of resin such as polyimide resin, or the like.

The insulating tube 25 made of polyimide resin can smoothly slide relative to the internal electrical cable 2 or the flexible wiring substrate 30 at low friction, it is thereby preferable.

An internal-conductor-connection portion 37a (cable connection portion) at which the internal conductor 2a of the built-in electrical cable 2 is soldered on the internal conductor terminal 34c and an external-conductor-connection portion 37b (cable connection portion) at which the external conductor 2b of the built-in electrical cable 2 is soldered on the external conductor terminal 34d are formed at the rear portion 34 of the flexible wiring substrate 30.

An internal-conductor-connection portion 37a (cable connection portion) at which the internal conductor 2a of the built-in electrical cable 2 is soldered on the internal conductor terminal 35c and an external-conductor-connection portion 37b (cable connection portion) at which the external conductor 2b of the built-in electrical cable 2 is soldered on the external conductor terminal 35d are formed at the rear portion 35 of the flexible wiring substrate 30.

The insulating tube 25 coats the internal-conductor-connection portion 37a and the external-conductor-connection portion 37b of the rear portions 34 and 35.

Furthermore, by cured resin 26 filling the inside of the insulating tube 25, the insulating tube 25 is fixed to and integrated with the flexible wiring substrate 30 and the built-in electrical cable 2 which are located inside the insulating tube 25.

As shown in FIG. 1, the lens-attached imaging module 11 includes a front-end imaging unit 12 accommodating the front-edge unit 110 together with a lens unit 24 (field lens unit) and a cover member 23 fixed to the imaging device 22 of the imaging module 11 in a sleeve-shaped metal frame member 41 having, for example, a circular cylindrical shape or the like.

The cover member 23 is a plate-shaped transparent member covering a light-receiving face 21a of the imaging unit 21 of the front-edge unit 110 (refer to FIG. 2).

The lens unit 24 is configured to include a cylinder-shaped lens barrel 24a into which an object lens (not shown in the figure) is incorporated.

The lens unit 24 is provided so that an optical axis is positioned at the light-receiving face 21a of the imaging unit 21 and an end of the lens barrel 24a in the direction of the axis thereof is fixed to the cover member 23.

The lens unit 24 provides an image onto the light-receiving face 21a of the imaging device 12 based on light guided from the front side of the front-end imaging unit 12 through the lens provided in the lens barrel 24a. Additionally, the front-end imaging unit 12 is configured to accommodate the front ends of the built-in electrical cables 2, which are respectively connected to the two rear portions 34 and 35 of the flexible wiring substrate 30, together with the front-edge unit 110, in the metal frame member 41.

In the lens-attached imaging module 11 shown in FIG. 1 as an example, an end of the electrical cable 1 (an end of the part covered with the outer coating 3) is disposed outside the metal frame member 41.

The built-in electrical cable 2 extending from an front end the outer coating 3 of the electrical cable 1 is drawn into the metal frame member 41 through an rear edge on the opposite side of the front edge accommodating the lens unit 24 of the metal frame member 41.

The metal frame member 41 is adhesively-fixed to the insulating tube 25 of the imaging module 10 by cured resin 27 filling the inside of the metal frame member 41.

The insulating tube 25 of the imaging module 10 prevents the internal-conductor-connection portion 37a and the external-conductor-connection portion 37b respectively formed at the two rear portions 34 and 35 of the flexible wiring substrate 30 from being short-circuited as a result of coming into contact with the metal frame member 41.

The flexible wiring substrate 30 of the imaging module 10 will be described in detail.

As shown in FIG. 1, the rear portion 34 of the flexible wiring substrate 30 includes an extended portion 34e inclined at a sharp angle with respect to the device-mounted portion 32 and a connection end portion 34f extending from the extended portion 34e to the back side thereof.

Similarly, the rear portion 35 of the flexible wiring substrate 30 includes an extended portion 35e inclined at a sharp angle with respect to the device-mounted portion 32 and a connection end portion 35f extending from the extended portion 35e to the back side thereof.

The extended portions 34e and 35e are inclined at a sharp angle with respect to a mount back face 32b on a side opposite to the mount face 32a of the device-mounted portion 32.

The extended portions 34e and 35e of the two rear portions 34 and 35 of the flexible wiring substrate 30 come close to each other in the direction to the backward of the device-mounted portion 32 from ends which are located at both sides the device-mounted portion 32 in the longitudinal direction of the substrate (vertical direction in FIG. 1).

The flexible wiring substrate 30 shown as an example includes an extended tail portion 38 at which the opposed faces 34a and 35a are in contact with each other and the connection end portions 34f and 35f of the two rear portions 34 and 35 align in the longitudinal direction thereof.

The two rear portions 34 and 35 are adhesively-fixed to each other by resin 39, and the resin fills a triangle-inner space 31 (hereinafter, referred to as a gap between the extended portions) surrounded by the device-mounted portion 32, the extended portions 34e and 35e located at both sides of the device-mounted portion 32, and the extended tail portion 38.

In the flexible wiring substrate 30, the connection end portions 34f and 35f are adhesively-fixed to each other by injecting the resin 39 into at least a front edge (end close to the device-mounted portion 32) between the connection end portions 34f and 35f constituting the extended tail portion 38.

According to this configuration, the rear portions 34 and 35 are reliably adhesively-fixed to each other, and the shape stability of the flexible wiring substrate 30 increases.

Moreover, in the flexible wiring substrate 30, the rear portions 34 and 35 are not adhesively-fixed to each other, and a constitution can be adopted in which a portion having flexibility is ensured between the portion at which the extended portions 34e and 35e are adhesively-fixed to each other and the portion at which the connection end portions 34f and 35f are adhesively-fixed to each other.

In this constitution, for example, the portions separated from the extended portions 34e and 35e of the connection end portions 34f and 35f are adhesively-fixed to each other, the rear portions 34 and 35 are not adhesively-fixed to each other, and the portion having flexibility is ensured between the portion at which the extended portions 34e and 35e are adhesively-fixed to each other and the portion at which the connection end portions 34f and 35f are adhesively-fixed to each other.

In this constitution, there is an advantage in that it is possible to carry out adjustment of the optical axis of the imaging unit 21 on the imaging device 22 by deforming the flexible portion of the flexible wiring substrate 30 located between the portion at which the extended portions 34e and 35e are adhesively-fixed to each other and the portion at which the connection end portions 34f and 35f are adhesively-fixed to each other, after the front-edge unit 110 is assembled.

In the flexible wiring substrate 30, due to the cured resin 39 filling the gap between the extended portions 31, the configuration of the portion located around the gap between the extended portions 31 is detained, deformation is less easily generated, and the shape stability thereof is ensured.

In the case of using the flexible wiring substrate 30, the configuration of the front edge configured by the device-mounted portion 32 and the extended portions 34e and 35e located at both sides of the device-mounted portion 32 can be stably maintained by the cured resin 39 implanted into the gap between the extended portions 31.

For this reason, in the imaging module 10, when the front-end imaging unit 12 (refer to FIG. 1) is assembled by accommodating the front-edge unit 110 in the metal frame member 41, it is possible to easily adjust the positions and directions of the imaging unit 21 and the lens unit 24 relative to the metal frame member 41 with a high level of accuracy.

The flexible wiring substrate 30 has a structure having two extended portions 34e and 35e which bend from the device-mounted portion 32 at both sides of the device-mounted portion 32 and which are extended so as to come close to each other with increasing distance from the device-mounted portion 32, and ensuring the space 31 which is between the extended portions 34e and 35e and which is filled with the resin 39.

According to the flexible wiring substrate 30, as a result of the structure having the two extended portions 34e and 35e which are extended so as to come close to each other with increasing distance from the device-mounted portion 32, it is possible to ensure a high level of shape stability as compared with, for example, a structure having a pendent device-mounted portion having a cantilever shape such as Japanese Unexamined Patent Application, First Publication No. 2009-260553 and Japanese Unexamined Patent Application, First Publication No. 2008-227733.

In addition, in the case of using the flexible wiring substrate 30, it is possible to ensure a more high level of shape stability by adhesively-fixing the extended portions 34e and 35e to each other with the cured resin 39 filling the gap between the extended portions 31.

The imaging module 10 shown as an example includes a structure in which conductors of the built-in electrical cable 2 are soldered on the terminals of the external face sides (the positions of the outer surfaces 34b and 35b) of the connection end portions 34f and 35f connected to each other.

Because of this, the length of the front-edge unit 110 in the width direction thereof, that is a direction of the gap between the bend portions 30d located at both sides of the device-mounted portion 32, can be minimized.

Accordingly, the imaging module 10 effectively contributes to reduction in the diameter (fine diameter) of the front-end imaging unit 12 assembled by fixing and inserting the front-edge unit 110 into the metal frame member 41.

Figure 17:
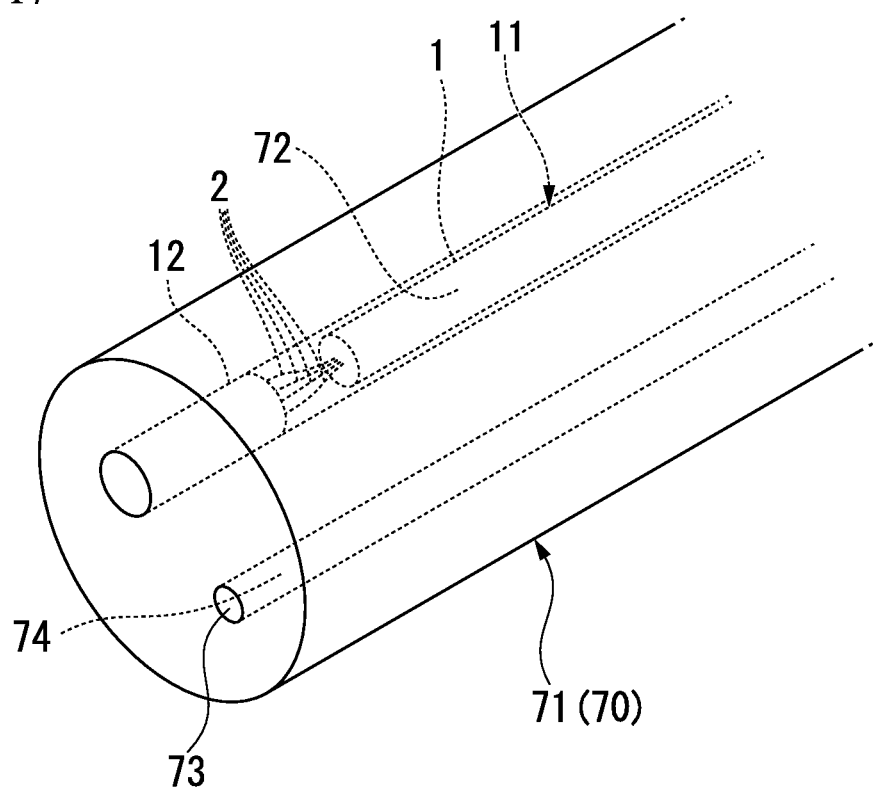
FIG. 17 is a view illustrating an endoscope of an embodiment related to the invention and is an enlarged perspective view showing a tube front edge of the endoscope.

Furthermore, as shown in FIG. 17, the imaging module 10 effectively contributes to reduction in the diameter (fine diameter) of an endoscope 70 in which the lens-attached imaging module 11 is housed in a lumen 72 of an insertion portion 71.

In the structure of the endoscope 70 as shown in FIG. 17, the insertion portion 71 includes a lumen 74 (second lumen) in which an optical fiber 73 used for illuminating light (use for light guide) is accommodated as well as the lumen 72 (first lumen) in which the lens-attached imaging module 11 is accommodated.

Particularly, the inventors manufactured the lens-attached imaging module 11 as a prototype by use of a tabular imaging device 22 having 0.75 mm square, a polyimide insulating tube 25 having an outer diameter of 1.05 mm, and a circular-cylindrical shaped metal frame member 41 having an outer diameter of 1.2 mm.

Additionally, the outer diameter of the insertion portion of an endoscope manufactured as a prototype by use of the lens-attached imaging module 11 was 5 mm.

Moreover, according to the imaging module 10, even where a member (shape-retaining member) which is attached to the flexible wiring substrate and maintains the configuration of the imaging module, such as a block disclosed in Japanese Unexamined Patent Application, First Publication No. 2011-217887, is not used, it is possible to ensure sufficient shape stability at the front edge of the flexible wiring substrate 30 by the resin 39 filling the gap between the extended portions 31.

Since a shape-retaining member is not necessary, it is possible to efficiently manufacture the imaging module 10 at a low cost.

As a result of using, for example, flexible wiring substrate formation apparatus 50 (hereinafter, referred to as substrate formation apparatus) shown in FIGS. 7A and 7B, it is possible to effectively assemble the imaging module 10.

Figure 7A:
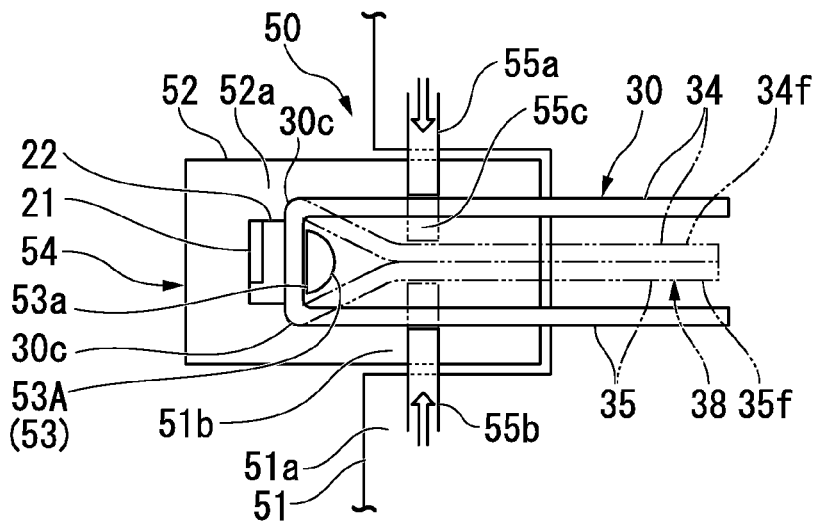
FIG. 7A is a plan view illustrating a flexible wiring substrate formation apparatus of an embodiment related to the invention.
Figure 7B:
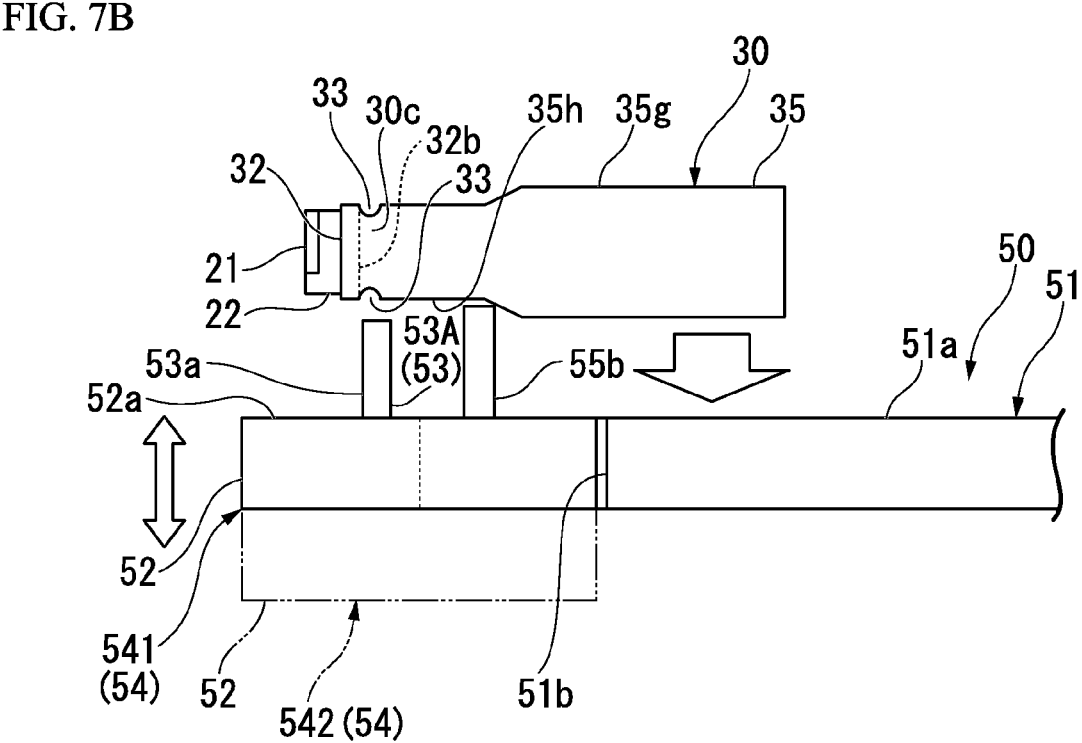
FIG. 7B a side view illustrating the flexible wiring substrate formation apparatus of the embodiment related to the invention.

The substrate formation apparatus 50 shown in FIGS. 7A and 7B is configured to include: a flexible-wiring-substrate mounting stage 51 (hereinafter, referred to as substrate mounting stage) on which the flexible wiring substrate 30 is to be mounted; and a pin-attached elevating stage 54 provided with a pin 53 protruding from an elevating stage 52 capable of moving up and down relative to the substrate mounting stage 51.

Additionally, the substrate formation apparatus 50 is configured to include a pair of movable pressing members 55a, 55b which is provided on the substrate mounting stage 51 and which can open and close in accordance with sliding motion along an upper face 51a of the substrate mounting stage 51. The elevating stage 52 of the pin-attached elevating stage 54 of the substrate formation apparatus 50 shown in FIGS. 7A and 7B as an example is guided by an inner face of an elevating stage race 51b which is depressed from the side face of the substrate mounting stage 51 and which extends in a vertical direction thereof, and the elevating stage moves up or down by a manual operation or by an automatic operation depending on the control of a switch.

This pin-attached elevating stage 54 is upward or downward movable to an initial position 541 (position indicated by a solid line in FIG. 7B) at which the upper face 52a of the elevating stage 52 substantially coincides with the upper face 51a of the substrate mounting stage and to a safety position 542 (position indicated by an ideal line in FIG. 7B) displaced downward from the initial position 541.

At the safety position 542, an upper edge of the pin 53 of the pin-attached elevating stage 54 is located at the same plane as that of the upper face 51a of the substrate mounting stage or at lower than the upper face 51a of the substrate mounting stage (lower side in FIG. 7B), and the pin 53 does not protrude from the upper side of the upper face 51a of the substrate mounting stage.

The initial position 541 is the upper limit position of the pin-attached elevating stage 54, and the safety position 542 is the lower limit position of the pin-attached elevating stage 54.

In accordance with sliding motion along the upper face 51a of the substrate mounting stage 51, the pair of movable pressing members 55a and 55b are movable from an open position indicated by a solid line in FIG. 7A to a close position at which the pressing members close to each other.

The pair of movable pressing members 55a and 55b move in the direction from the open position to the close position (closing operation) and thereby can sandwich the pair of rear portions 34 and 35 of the flexible wiring substrate 30 therebetween.

Additionally, the pair of movable pressing members 55a and 55b may define the position, at which the pair of rear portions 34 and 35 of the flexible wiring substrate 30 are sandwiched therebetween, as a close position, and the pressing members strict movement from the close position in a direction in which the separated distance therebetween contracts.

The closing operation of the pair of movable pressing members 55a and 55b and the movement (opening operation) from a closed state where the pair of rear portions 34 and 35 of the flexible wiring substrate 30 are sandwiched therebetween to the open position are carried out by a manual operation or by an automatic operation depending on the control of a switch.

Furthermore, the opening operation and the closing operation of the pair of movable pressing members 55a and 55b are coordinately carried out to each other.

In the opening operation and the closing operation, the pair of movable pressing members 55a and 55b moves opposite directions to each other.

In the substrate formation apparatus 50 shown in FIG. 7A as an example, the movable pressing members 55a and 55b located at the open position are provided so as to protrude from an upside position of the substrate mounting stage 51 located at both sides in the groove direction of the elevating stage race 51b to an upside position of the upper face 52a of the elevating stage via the elevating stage race 51b opening at the peripheral portion of the upper face 51a of the substrate mounting stage.

The separated distance between the pair of movable pressing members 55a and 55b located at the open position is made substantially equal to the length in an extending direction which coincides with a direction of the gap between the rear portions 34 and 35 at the mount back face 32b of the device-mounted portion 32 of the flexible wiring substrate 30 shown in FIG. 1 or the like as an example.

As shown in FIG. 7A, the rear portions 34 and 35 of the flexible wiring substrate 30 can be easily inserted into the gap 55c between the pair of movable pressing members 55a and 55b in a state where the rear portions 34 and 35 extend in a direction perpendicular to the direction of the gap between the pair of movable pressing members 55a and 55b.

In particular, the direction in which the mount back face 32b extends coincides with the longitudinal direction of the flexible wiring substrate 30 (the longitudinal direction of the substrate) which is before bending (folding) as shown in FIG. 2. In the explanation described above or below, in the substrate formation apparatus 50 shown as an example, the direction of the gap between the pair of movable pressing members 55a and 55b is referred to as a width direction (vertical direction in FIG. 7A), and a direction perpendicular to a width direction along the upper face 51a of the substrate mounting stage (right and left directions in FIGS. 7A and 7B) is referred to as a front-back direction.

Furthermore, in the explanation regarding the substrate formation apparatus 50 shown as an example, the left side in FIGS. 7A and 7B is referred to as "front" (front side), the right side thereof is referred to as "back" (back side).

The pin 53 of the pin-attached elevating stage 54 is located at the position separated from the gap 55c between the pair of movable pressing members 55a and 55b to the front side in the front-back direction of the apparatus.

This pin 53 is located on a side opposite to the center region of the upper face 51a of the substrate mounting stage from the gap 55c between the pair of movable pressing members 55a and 55b.

A flat mounted-portion contacting face 53a is formed on the back face side (front side) of the pin 53 which is on the opposite side of the gap 55c between the pair of movable pressing members 55a and 55b, and the device-mounted portion 32 of the flexible wiring substrate 30 comes into contact with the mounted-portion contacting face.

This mounted-portion contacting face 53a is formed perpendicular to the front-back direction of the apparatus.

The width of the mounted-portion contacting face 53a is the same as the length in an extending direction which coincides with the direction of the gap between the rear portions 34 and 35 (coincident with the longitudinal direction of the flexible wiring substrate 30) in the mount back face 32b of the device-mounted portion 32 of the flexible wiring substrate 30 shown in FIG. 1 or the like as an example.

Furthermore, the mounted-portion contacting face 53a is entirely formed on the front side of the portion of the pin 53 located on the elevating stage 52.

Moreover, the cross section of the pin 53 (cross section perpendicular to a direction of an axis of the pin 53) is formed in a tapered shape so that the size of the pin 53 in the width direction thereof decreases with directed from the mounted-portion contacting face 53a toward the back side of the apparatus (right sides in FIGS. 7A and 7B).

Figure 18A:
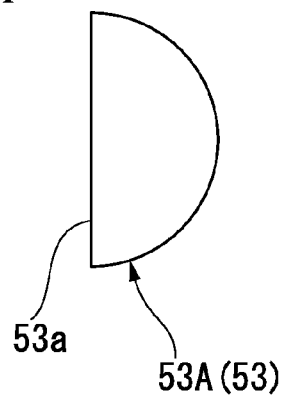
FIG. 18A is a view showing an example of a cross-sectional shape of a pin of the flexible wiring substrate formation apparatus shown in FIGS. 7A and 7B (cross-sectional configuration perpendicular to the axis line of the pin).

The pin 53 shown in FIGS. 7A and 18A (reference numeral thereof is 53A in the drawings) has a semicircle in cross-sectional shape which is perpendicular to the direction of the axis thereof.

The entire outer peripheral face of the pin 53A formed on a region from the mounted-portion contacting face 53a to the back side of the apparatus is a curved surface which curves and has an axis line parallel to the axis line of the pin 53A.

Figure 18B:
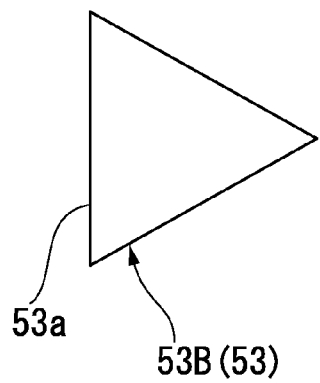
FIG. 18B is a view showing an example of a cross-sectional shape of a pin of the flexible wiring substrate formation apparatus shown in FIGS. 7A and 7B (cross-sectional configuration perpendicular to the axis line of the pin).

The structure of the pin 53 is not limited to the aforementioned structure, and, for example, a structure (pin 53B) may be adopted therefor whose cross-sectional shape perpendicular to the direction of an axis of the pin 53 is an acute-angled triangle protruding from the mounted-portion contacting face 53a to the back side of the apparatus as shown in FIG. 18B.

Figure 18C:
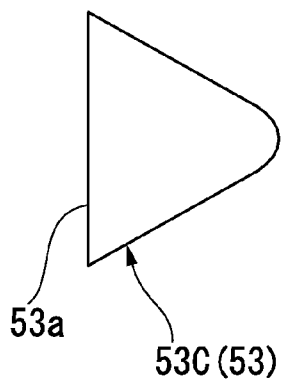
FIG. 18C is a view showing an example of a cross-sectional shape of a pin of the flexible wiring substrate formation apparatus shown in FIGS. 7A and 7B (cross-sectional configuration perpendicular to the axis line of the pin).

Additionally, a pin 53C or the like having cross-sectional configuration in which an apparatus-rear edge of the pin 53B is curved can be adopted (FIG. 18C).

This substrate formation apparatus 50 is preferably used for folding of the band-shaped flexible wiring substrate 30 shown in FIG. 2 (bending-shaping step) and adhesively-fixing of the two rear portions 34 and 35 to each other which are formed by the folding (adhesively-fixing step).

Here, an example of a method of manufacturing the imaging module 10, including a step of using the substrate formation apparatus 50, will be described.

At first, the imaging device 22 is mounted on the device-mounted portion 32 of the band-shaped flexible wiring substrate 30 shown in FIG. 2 (device mounting step).

Subsequently, a substrate mounting step is carried out in which the flexible wiring substrate 30 is mounted on the substrate mounting stage 51 and the flexible wiring substrate is mounted on the upper face 52a of the elevating stage of the pin-attached elevating stage 54 which is located at the initial position with respect to the substrate mounting stage 51, and the flexible wiring substrate 30 is thereby disposed in a state shown in FIG. 8.

The substrate mounting step is performed in a state where the pair of movable pressing members 55a and 55b are located at the open position.

Figure 8:
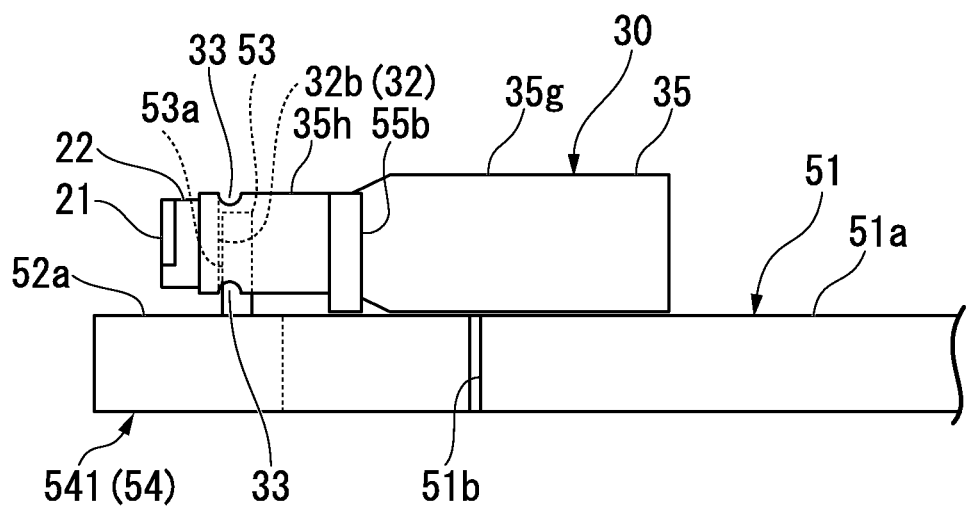
FIG. 8 is a view illustrating a step of a method of manufacturing an imaging module using the flexible wiring substrate formation apparatus shown in FIGS. 7A and 7B and showing a state where a substrate mounting step of mounting the flexible wiring substrate onto an elevating stage and onto a flexible-wiring-substrate mounting stage is completed.

As shown in FIG. 8, the substrate mounting step allows the device-mounted portion 32 of the flexible wiring substrate 30 (particularly, the mount back face 32a) to come into contact with the mounted-portion contacting face 53a of the pin 53 of the pin-attached elevating stage 54.

Furthermore, before the substrate mounting step, portions located at both sides of the device-mounted portion 32 in the longitudinal direction of the flexible wiring substrate 30 (the rear-portion-formation portions 340 and 350) bend from the device-mounted portion 32 (folding), and therefore the rear portions 34 and 35 are formed.

In the substrate mounting step, the rear portions 34 and 35 are inserted into the gap 55c between the pair of movable pressing members 55a and 55b.

Each of the rear portions 34 and 35 is inserted into the gap 55c so as to extend in a direction perpendicular to the direction of the gap between the pair of movable pressing members 55a and 55b.

As shown in FIG. 2, at both sides in the extending direction of the device-mounted portion 32 of the flexible wiring substrate 30, cut-off portions 33 are formed at both sides in the width direction (substrate width direction) orthogonal to the longitudinal direction of the flexible wiring substrate 30.

As shown in FIG. 8, in the substrate mounting step, the rear-portion-formation portions 340 and 350 located at both sides of the device-mounted portion 32 in the longitudinal direction of the flexible wiring substrate 30 bend from the device-mounted portion 32 while utilizing the cut-off portions 33 (folding), and therefore, it is possible to easily form the rear portions 34 and 35.

Furthermore, the imaging device 22 is almost entirely disposed on the mount face 32a serving as the front face of the device-mounted portion 32 and is integrated with the mount face 32a, and the imaging device restricts deformation of the device-mounted portion 32.

This structure effectively contributes to ease of operation of bending the rear-portion-formation portions 340 and 350 from device-mounted portion 32.

As shown in FIG. 2, in the flexible wiring substrate 30, the regions at which the cut-off portions 33 are formed in the substrate-longitudinal direction thereof are ease-deformation portions 30c having a width narrower than that of a region positioned at both sides of the regions.

The flexible wiring substrate 30 includes the constitution in which the ease-deformation portions 30c exist between the device-mounted portion 32 and the rear-portion-formation portions 340 and 350 located at both sides of the device-mounted portion 32.

Consequently, in the flexible wiring substrate 30, when the rear portions 34 and 35 bending with respect to the device-mounted portion 32 are formed as shown in FIGS. 1 and 7A, the ease-deformation portions 30c become the bend portions 30d.

Particularly, in FIG. 1, the rear portions 34 and 35 of the flexible wiring substrate 30 extend from the bend portions 30d located at both sides of the device-mounted portion 32 to the back side of the device-mounted portion 32.

In other cases, the cut-off portions 33 are not necessarily formed at both sides of the flexible wiring substrate 30 in the substrate width direction.

As the flexible wiring substrate 30, a structure may be adopted in which the cut-off portion 33 is only formed at one side in the substrate width direction at both sides in the extending direction of the device-mounted portion 32.

As shown in FIGS. 1 and 7A, the bend portions 30d located at both sides of the device-mounted portion 32 protrude from the range which faces the imaging device 22 of the device-mounted portion 32.

The bend portions 30d located at both sides of the device-mounted portion 32 shown as an example are formed by bending the ease-deformation portions 30c, and the ease-deformation portions 30c protrude from both sides of the range facing the imaging device 22 of the device-mounted portion 32 onto which the imaging device 22 is mounted (projection range of the imaging device).

In the structure in which the ease-deformation portions 30c are pendent from the device-mounted portion 32 and located at the positions which do not overlap the range facing the imaging device 22 of the device-mounted portion 32, the imaging device 22 does not interfere in the operation of forming the bend portions 30d by folding the ease-deformation portions 30c, and the bend portions 30d are smoothly formed.

Figure 3F:
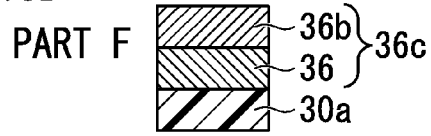
FIG. 3F is a view showing a cross-section structure of part F of the flexible wiring substrate shown in FIG. 2.
Figure 3G:
FIG. 3G is a view showing a cross-section structure of part G of the flexible wiring substrate shown in FIG. 2.
Figure 4:
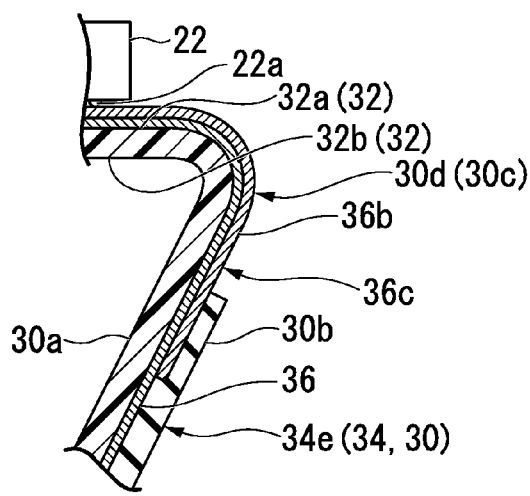
FIG. 4 is a view showing a cross-section structure in the vicinity of a bend portion of the flexible wiring substrate of the imaging module shown in FIG. 1 (position close to the bend portion).

As shown in FIGS. 2 to 4, in the flexible wiring substrate 30, of the wiring 36 formed on one surface side of an insulative base member 30a which is formed in a sheet shape and has an electrical insulating property, the portions located at the rear-portion-formation portions 340 and 350 are almost entirely covered with resin-coated layers 30b (coated layer, for example, solder resist) having electrical insulation stacked in layers on the insulative base member 30a.

Over the rear-portion-formation portions 340 and 350 of the flexible wiring substrate 30, the resin-coated layers 30b are almost entirely layered on the surface (wiring formation surface) on which the wiring 36 of the insulative base member 30a are formed.

The substantially entire rear-portion-formation portions 340 and 350 of the flexible wiring substrate 30 are coated portions having a constitution in which the resin-coated layer 30b is stacked in layers on one surface side of the insulative base member 30a.

On the other hand, the resin-coated layers 30b are not provided on the device-mounted portion 32 and the ease-deformation portions 30c, and the device-mounted portion and the ease-deformation portions are wiring exposed area 30e at which the wiring 36 are exposed (refer to FIG. 2 or the like).

Because of this, the ease-deformation portions 30c are bent easier than the rear-portion-formation portions 340 and 350.

Also, as shown in FIGS. 2 and 3A to 3G, the rear-portion-formation portion 340 includes a reinforced portion 34g which is located between the center region in the extending direction (the longitudinal direction of the substrate) and the portion opposite to the device-mounted portion 32 (portion between the center region and both ends of the substrate).

Similarly, the rear-portion-formation portion 350 includes a reinforced portion 35g which is located between the center region in the extending direction (the longitudinal direction of the substrate) and the portion opposite to the device-mounted portion 32 (portion between the center region and both ends of the substrate).

In the layered structure of the reinforced portion 34g, a sheet-shaped reinforcing member 30g is attached to the face on a side opposite to the wiring formation surface of the insulative base member 30a with an adhesive layer 30f interposed therebetween, and the sheet-shaped reinforcing member 30g is thereby integrated with the reinforced portion 34g.

Similarly, in the layered structure of the reinforced portion 35g, a sheet-shaped reinforcing member 30g is attached to the face on a side opposite to the wiring formation surface of the insulative base member 30a with an adhesive layer 30f interposed therebetween, and the sheet-shaped reinforcing member 30g is thereby integrated with the reinforced portion 35g.

The sheet-shaped reinforcing member 30g does not coat a portion (area) between the reinforced portion 34g of the rear-portion-formation portion 340 and the device-mounted portion 32, a portion (area) between the reinforced portion 35g of the rear-portion-formation portion 350 and the device-mounted portion 32, the ease-deformation portion 30c, and the device-mounted portion 32.

The terminals 34c and 34d are placed on the reinforced portion 34g.

The terminals 35c and 35d are placed on the reinforced portion 35g.

A non-reinforced extending portion 34h located between the reinforced portion 34g of the rear-portion-formation portion 340 of the flexible wiring substrate 30 and the device-mounted portion 32 is bent easier than the reinforced portion 34g, and the ease-deformation portion 30c is bent easier than the non-reinforced extending portion 34h of the rear-portion-formation portion 340.

Similarly, a non-reinforced extending portion 35h located between the reinforced portion 35g of the rear-portion-formation portion 350 of the flexible wiring substrate 30 and the device-mounted portion 32 is bent easier than the reinforced portion 35g, and the ease-deformation portion 30c is bent easier than the non-reinforced extending portion 35h of the rear-portion-formation portion 350.

Moreover, the reinforced portion 34g is used as a part constituting the connection end portion 34f of the rear portion 34 of the flexible wiring substrate 30 which is shaped by folding as shown in FIG. 1 (refer to FIGS. 1 and 7A).

Similarly, the reinforced portion 35g is used as a part constituting the connection end portion 35f of the rear portion 35 of the flexible wiring substrate 30 which is shaped by folding as shown in FIG. 1 (refer to FIGS. 1 and 7A).

Furthermore, the extended portion 34e of the flexible wiring substrate 30 which is shaped by folding as shown in FIG. 1 is formed of the non-reinforced extending portion 34h.

Similarly, the extended portion 35e of the flexible wiring substrate 30 is formed of the non-reinforced extending portion 35h.

Additionally, as shown in FIG. 2, the reinforced portion 34g of the rear-portion-formation portion 340 of the flexible wiring substrate 30 is formed wider than the non-reinforced extending portion 34h of the rear-portion-formation portion 340.

The reinforced portion 35g of the rear-portion-formation portion 350 of the flexible wiring substrate 30 is formed wider than the non-reinforced extending portion 35h of the rear-portion-formation portion 350.

It is clear from the above structure that, in two rear-portion-formation portions 340 and 350 of the flexible wiring substrate 30, the non-reinforced extending portions 34h and 35h are bent easier than the reinforced portions 34g and 35g.

In addition, an end which is close to the reinforced portion 34g at the non-reinforced extending portion 34h of the rear-portion-formation portion 340 is a tapered portion, and the width dimension of the tapered portion increases with the approach of the reinforced portion 34g.

Similarly, an end which is close to the reinforced portion 35g at the non-reinforced extending portion 35h of the rear-portion-formation portion 350 is a tapered portion, and the width dimension of the tapered portion increases with the approach of the reinforced portion 35g.

In FIG. 2, the resin-coated layers 30b are formed so as to avoid the terminals 34c, 34d, 35c, and 35d of the rear-portion-formation portions 340 and 350.

Accordingly, the terminals 34c, 34d, 35c, and 35d are not coated with the resin-coated layers 30b.

A surface (terminal surface) on the opposite side of the insulative base member 30a is exposed to the surface side of the resin-coated layers 30b of the rear-portion-formation portions 340 and 350.

Particularly, as shown in FIG. 3A, terminal-passivation plating 36e made of gold or the like, which are formed on surfaces of pads 36d formed integrally with the wirings 36 and on the opposite side of the insulative base member 30a, are formed on the terminals 34c, 34d, 35c, and 35d shown as an example.

Terminal surfaces on a side opposite to the insulative base member 30a of the terminals 34c, 34d, 35c, and 35d are formed of the terminal-passivation plating 36e.

As a material used to form the terminal-passivation plating 36e, a material having excellent solder adhesion such as gold or the like described above may be adopted.

However, as the terminals 34c, 34d, 35c, and 35d, a constitution can be adopted in which the pads 36d are only formed without forming the terminal-passivation plating 36e.

Additionally, as shown in FIGS. 2 to 4, of the wirings 36 of the flexible wiring substrate 30, a wiring exposed area 30e and portions located at end portions close to the device-mounted portion 32 of the rear-portion-formation portions 340 and 350 are passivation-plating-coated wiring 36c covered with passivation plating 36b formed on the top face thereof.

As the flexible wiring substrate 30, a substrate is used including a structure in which, for example, the passivation plating 36b formed of a metal material providing excellent extensibility such as gold-plated or the like are formed on the wiring 36 made of copper (copper wiring).

According to this configuration, wire breakage or the like is less easily generated at portions in the wiring 36, which are located at the ease-deformation portions 30c or the bend portions 30d.

Consequently, the ease-deformation portions 30c and the bend portions 30d of the flexible wiring substrate 30 can be folded easier than the non-reinforced extending portions 34h and 35h, and breakage of the wiring 36 is less easily generated.

After completion of the substrate mounting step, a bending-shaping step is performed of carrying out an operation of closing the pair of movable pressing members 55a and 55b located at the open position, folding the rear portions 34 and 35 from the device-mounted portion 32, forming the extended portion 34e at the rear portion 34, and forming the extended portion 35e at the rear portion 35.

Here, in order to obtain the flexible wiring substrate 30 having the configuration shown in FIGS. 1 and 5A, the movable pressing members 55a and 55b sandwich the pair of rear portions 34 and 35 of the flexible wiring substrate 30 therebetween.

The pair of movable pressing members 55a and 55b are positioned at ends of the reinforced portions 34g and 35g of the non-reinforced extending portions 34h and 35h of the rear portions 34 and 35 and sandwich the pair of rear portions 34 and 35 therebetween.

The pair of movable pressing members 55a and 55b are aligned so as not to sandwich the reinforced portions 34g and 35g therebetween.

In this way, at the rear portions 34 and 35 of the flexible wiring substrate 30, the opposed faces 34a and 35a are connected to each other.

At this time, the extended portion 34e and the connection end portion 34f are formed at the rear portion 34 and the extended portion 35e and the connection end portion 35f are formed at the rear portion 35 in the flexible wiring substrate 30 as a result of the relationship between the length of the pin 53 in the width direction of the mounted-portion contacting face 53a and the separated distance between the pair of movable pressing members 55a and 55b.

Furthermore, the triangle gap between the extended portions 31 is formed at the front edge of the fold-shaped flexible wiring substrate 30 (fold-shaping finished substrate).

The pin 53 of the substrate formation apparatus 50 is inserted into the gap between the extended portions 31 of the flexible wiring substrate 30 (fold-shaping finished substrate).

As shown in FIGS. 2 and 6, the width dimension W1 of the reinforced portion 34g of the first rear portion 34 of the flexible wiring substrate 30 is slightly greater than the width dimension W2 of the reinforced portion 35g of the second rear portion 35.

With this configuration, for example, as shown in FIG. 6, the first rear portion 34 and the second rear portion 35 can be easily connected together in the flexible wiring substrate 30 while the reinforced portion 35g of the second rear portion 35 is positioned relative to the reinforced portion 34g of the first rear portion 34 so as not to protrude from the reinforced portion 34g of the first rear portion 34 in the width direction thereof.

This is effective in terms of reliably preventing an unnecessary increase in the length of the extended tail portion 38 in the width direction thereof (the length in the vertical direction in FIG. 6), effectively contributing to a reduction in the diameter of the front-end imaging unit 12 of the lens-attached imaging module 11 (downsizing of diameter).

Figure 9:
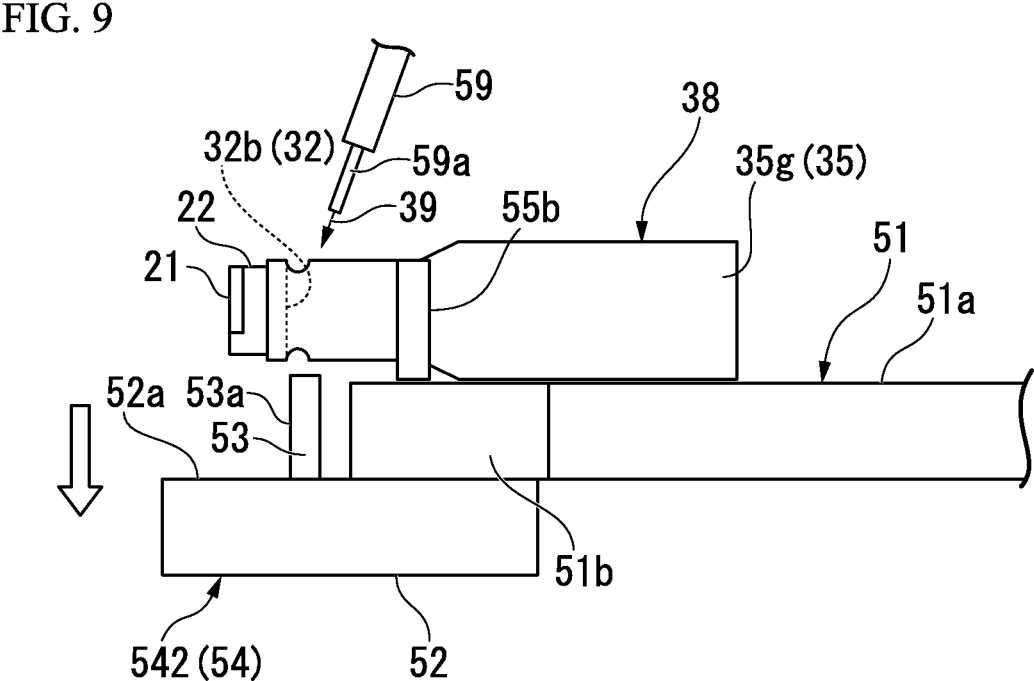
FIG. 9 is a view illustrating a step of a method of manufacturing an imaging module using the flexible wiring substrate formation apparatus shown in FIGS. 7A and 7B and is a view illustrating a step of filling, with resin, a space surrounded by a device-mounted portion of the flexible wiring substrate and extended portions that are located at both sides of the flexible wiring substrate after the step shown in FIG. 8.

After the bending-shaping step is completed, while maintaining a state where the pair of rear portions 34 and 35 of the flexible wiring substrate 30 (fold-shaping finished substrate) are sandwiched between the pair of movable pressing members 55a and 55b as shown in FIG. 9, the pin-attached elevating stage 54 moves downward from the initial position to the safety position, and the pin 53 is detached from the gap between the extended portions 31 of the flexible wiring substrate 30 (pin-detachment step).

Subsequently, the gap between the extended portions 31 of the flexible wiring substrate 30 is filled with the resin 39, this resin 39 is cured, and the rear portions 34 and 35 are adhesively-fixed to each other (adhesively-fixing step).

As shown in FIG. 9, the gap between the extended portions 31 of the flexible wiring substrate 30 can be efficiently filled with the resin 39 by use of, for example, an injector 59 provided with a nozzle portion 59a having an end which is insertable into the gap between the extended portions 31.

As the resin 39, a curable resin is adopted capable of allowing the rear portions 34 and 35 to be adhesively-fixed to each other due to curing.

As the resin 39, for example, a dry-curable resin; a multi-liquid reactive resin such as a two-liquid reactive resin or the like; a moisture-curable resin; a photo-curable resin such as an ultraviolet curable resin or the like; a thermosetting resin which is curable by heating, or the like can be adopted.

Additionally, a resin having a viscosity of 4000 to 7000 cps can be preferably used as the resin 39.

As a preferred example of the resin 39, a thermosetting epoxy resin can be adopted.

After completion of the adhesively-fixing step, the pair of movable pressing members 55a and 55b of the substrate formation apparatus 50 is opened by the opening operation, the flexible wiring substrate 30 (fold-shaping finished substrate) is removed from the substrate formation apparatus 50.

Thereafter, a cable connecting step of solder-mounting conductors of the built-in electrical cable 2 (the internal conductor 2a and the external conductor 2b) onto the terminals 34c, 34d, 35c, and 35d of the removed flexible wiring substrate 30 (fold-shaping finished substrate) is carried out.

Subsequently, as shown in FIG. 5A, the insulating tube 25, which is externally fitted onto the electrical cable 1 (or the built-in electrical cable 2 extended from the end of the outer coating thereof) in advance, moves toward the front side of the flexible wiring substrate 30 (the device-mounted portion 32 side).

Because of this, as shown in FIGS. 5B and 6, the extended tail portion 38 of the flexible wiring substrate 30 (fold-shaping finished substrate) together with the front end of the built-in electrical cable 2 and conductive connectors (the internal-conductor-connection portion 37a and the external-conductor-connection portion 37b) is entirely housed in the insulating tube 25.

Subsequently, as shown in FIG. 5B, as a result of injecting the resin 26 into the inside of the insulating tube 25, filling it, and curing the resin, the insulating tube 25 is adhesively-fixed to and integrated with the flexible wiring substrate 30 and the front end of the built-in electrical cable 2.

Hereinbelow, the step is also referred to as tube adhesion step, which accommodates the entirety of extended tail portion 38, the front end of the built-in electrical cable 2, and the conductive connectors in the insulating tube 25; fills the inside of the insulating tube 25 with the resin 26; and adhesively-attaches the contents (the flexible wiring substrate 30 or the like), which are accommodated in the insulating tube 25, to the insulating tube 25 to be integrated into a body.

Moreover, in the method of manufacturing the imaging module 10 (assembling method), a step is also carried out of fixing and attaching the lens unit 24 to the imaging device 22 to which the cover member 23 is preliminarily attached.

As long as the timing of performing the attachment step of the lens unit 24 is after completion of the device mounting step of mounting the imaging device 22 mounted on the device-mounted portion 32 of the flexible wiring substrate 30, the attachment step can be carried out at any time and the timing thereof is not particularly limited.

The assembling of the imaging module 10 completes when the attachment step of the lens unit 24 and the tube adhesion step are completed.

In the method of manufacturing the imaging module 10 (assembling method), instead of the carrying out of the device mounting step before the substrate mounting step, the device mounting step of mounting the imaging device 22 onto the device-mounted portion 32 may be carried out on or after the completion of the substrate mounting step.

In the method of manufacturing the imaging module 10, the timing of performing the device mounting step is only necessary to be previous to the attachment step of the lens unit 24.

In addition, the extended portions 34e and 35e may be adhesively-fixed to each other after filling the inside region surrounded by the two extended portions 34e and 35e and the device-mounted portion 32 with resin.

Furthermore, the extended portions 34e and 35e may be adhesively-fixed to each other before filling the inside region surrounded by the two extended portions 34e and 35e and the device-mounted portion 32 with resin.

According to the method of manufacturing the imaging module 10 of the embodiment related to the invention, it is possible to ensure the shape stability of the flexible wiring substrate 30 without using a shape-retaining member disclosed in such Japanese Unexamined Patent Application, First Publication No. 2011-217887.

Additionally, in this manufacturing method, time and effort for positioning the flexible wiring substrate with respect to the shape-retaining member in the case of using the shape-retaining member are not necessary.

Consequently, according to this manufacturing method, it is possible to easily and inexpensively obtain the flexible wiring substrate 30 (fold-shaping finished substrate) with a high level of the shape stability of the device-mounted portion 32 and the adjacent portion thereof (the front edge of the flexible wiring substrate 30 and the position close to the device-mounted portion 32).

Figure 15:
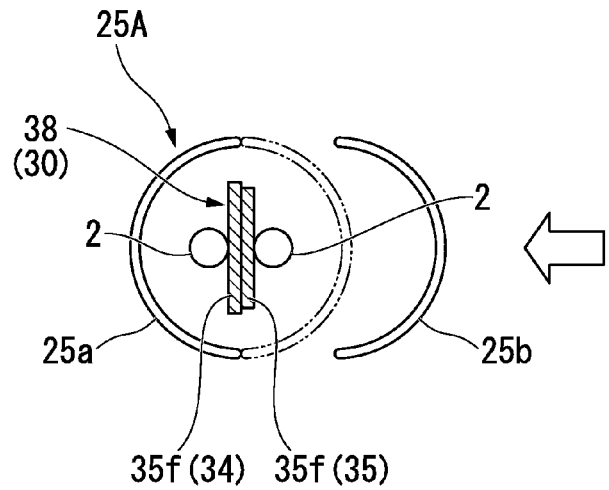
FIG. 15 is a view showing an insulating tube of another embodiment having a half-divided structure.

The insulating tube is not limited to the cylinder-shaped tube (refer to FIG. 6), a tube (insulating tube 25A) having a half-divided structure can be adopted, and the structure is assembled by, for example, connecting a pair of tube divided bodies 25a and 25b to each other so as to integrate the tube divided bodies into a body shown in FIG. 15.

As the pair of the tube divided bodies 25a and 25b, tube divided bodies made of resins such as polyimide or the like can be used as with the insulating tube 25 described above.

The insulating tube 25A having the half-divided structure is assembled in a cylindrical shape as a result of integrating the tube divided bodies 25a and 25b due to, for example, adhesive fixation by use of an adhesive, thermal welding, or the like.

In the case of using this the insulating tube 25A having the half-divided structure, when an operation of accommodating the extended tail portion 38 of the flexible wiring substrate 30 in the tube is carried out, it is not necessary to slide the tube from the back side to the front side relative to the flexible wiring substrate 30, unlike the insulating tube 25 that is a tubular integral molding.

In the case of using the insulating tube 25A, since the assembling can be realized by integrating and connecting the pair of the tube divided bodies 25a and 25b to each other, there is an advantage in that discouragement can be avoided such that sliding motion with respect to the flexible wiring substrate 30 causes the conductive connectors (the internal-conductor-connection portion 37a and the external-conductor-connection portion 37b) to come into contact with the tube and the tube to be thereby cleaved.

The imaging module 10 shown in FIG. 1 as an example includes a structure in which the entire extended tail portion 38 of the flexible wiring substrate 30 is accommodated in the insulating tube 25 by the resin 26 and is adhesively-integrated into a body.

The imaging module of the embodiment related to the invention is not limited to the imaging module having the aforementioned structure.

Figure 10:
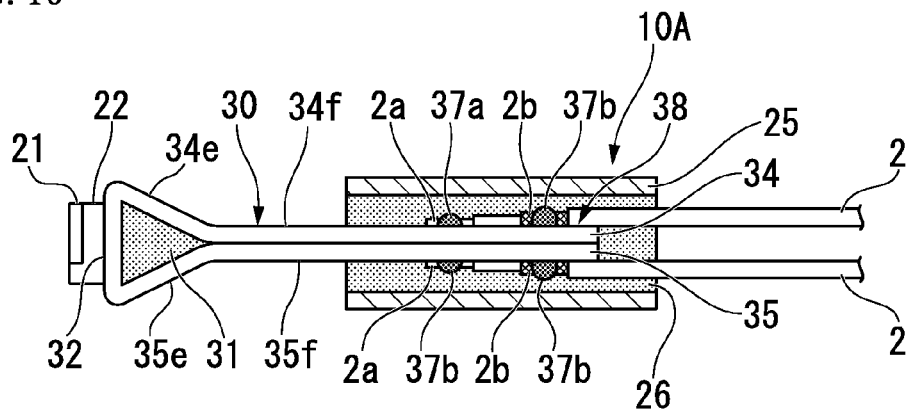
FIG. 10 is a cross-sectional view showing a structure of an imaging module of an embodiment related to the invention, in which a forward end of the insulating tube is located at position. The position is separated from the extended portions of the flexible wiring substrate to the rear side thereof and is separated from an internal-conductor-connection portion to the front side thereof.
Figure 11:
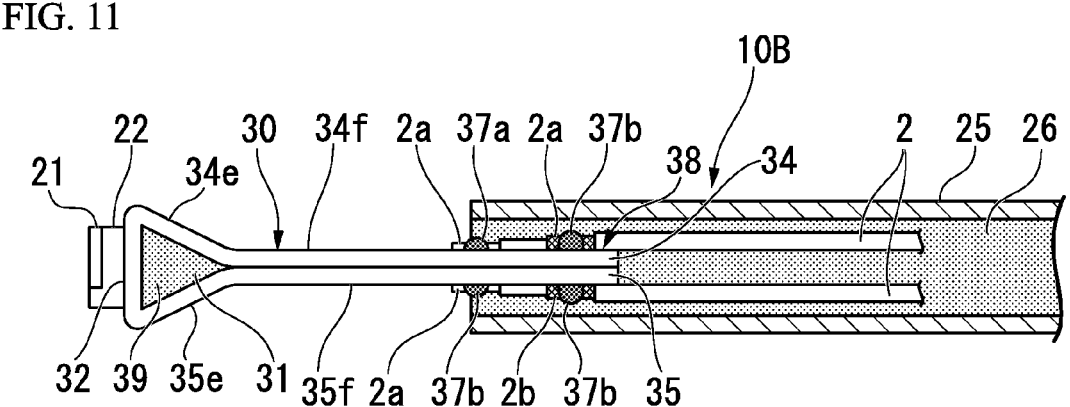
FIG. 11 is a cross-sectional view showing a structure of an imaging module of an embodiment related to the invention, in which a forward end of the insulating tube is positioned at an internal-conductor-connection portion of a connection end portion of the flexible wiring substrate and part of the internal-conductor-connection portion is exposed.

For example, as shown in FIGS. 10 and 11, the position of the insulating tube 25 in the front-back direction of the imaging module (right and left direction in FIGS. 10 and 11) relative to the flexible wiring substrate 30 (fold-shaping finished substrate) is variable.

In FIGS. 10 and 11, the extended tail portion 38 is accommodated in the insulating tube 25 arranged separately from the extended portion 35e of the rear portions 34 and 35 to the back side thereof.

In the insulating tube 25 of an imaging module 10A shown in FIG. 10, the front edge of the insulating tube 25 is disposed in the front side of the internal-conductor-connection portion 37a of the rear portions 34 and 35.

An insulating tube 25 of an imaging module 10B shown in FIG. 11 covers a part of the internal-conductor-connection portion 37a of the rear portions 34 and 35.

The position in the front-back direction of the insulating tube 25 relative to the flexible wiring substrate 30 is adjusted so that the front edge of the insulating tube 25 is placed at the position in the front side of the covered part (the position which is not covered with the insulating tube 25).

Particularly, only in terms of the position at which the insulating tube 25 is placed relative to the flexible wiring substrate 30 in the front-back direction, the imaging modules 10A and 10B shown in FIGS. 10 and 11 are comparatively different from the imaging module 10 shown in FIG. 1.

Figure 12:
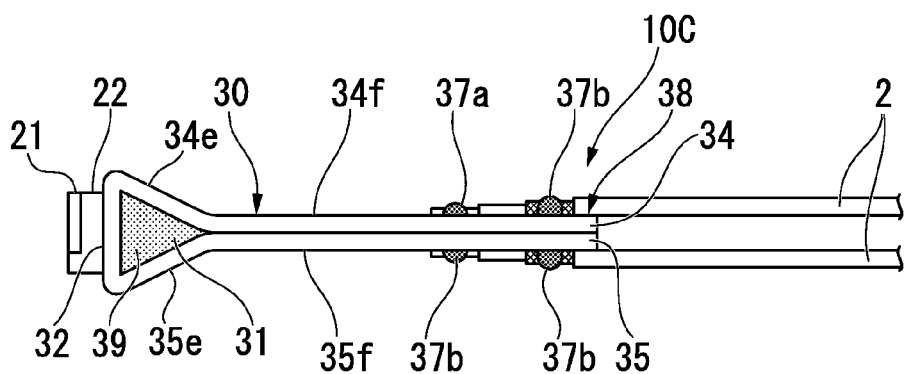
FIG. 12 is a side view showing an imaging module of an embodiment related to the invention which does not have an insulating tube.

Additionally, as an imaging module of an embodiment related to the invention, a structure (imaging module 10C) in which the insulating tube is omitted can be adopted as shown in FIG. 12.

An endoscope of an embodiment related to the invention includes a constitution in which the imaging module of the embodiment related to the invention together with a lens unit fixed to the imaging device is accommodated in a sleeve-shaped metal frame member.

The imaging module is not particularly limited as long as the imaging module of the embodiment related to the invention is adopted.

As the imaging module accommodated in the metal frame member of the endoscope, the imaging modules 10A, 10B, and 10C disclosed in FIGS. 11 and 12 can be adopted as well as the imaging module 10 shown in FIG. 1 or the like.

Figure 16:
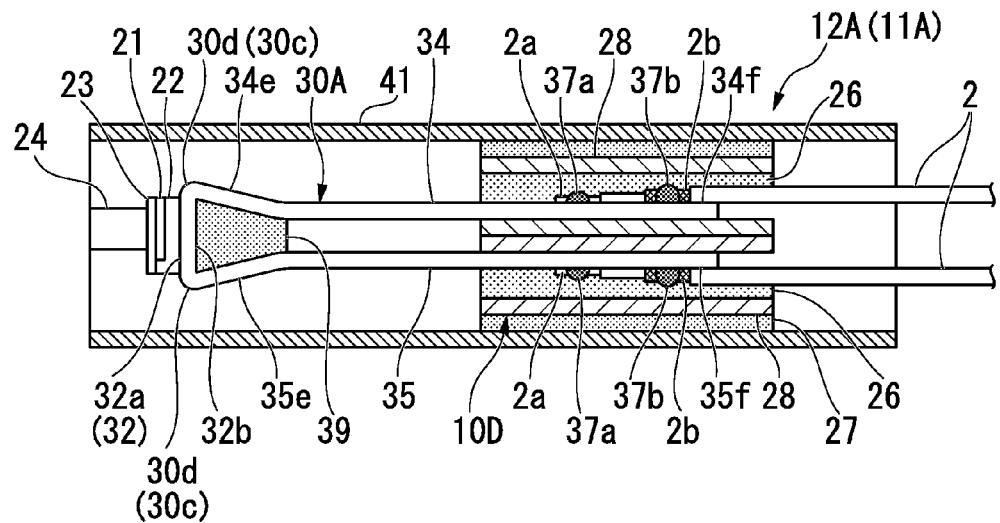
FIG. 16 is a cross-sectional side view showing an imaging module of an embodiment related to the invention having a structure in which insulating tubes are externally fitted onto and adhesively-integrated with two rear portions of a flexible wiring substrate, respectively.

In the imaging module 10D shown in FIG. 16, insulating tubes 28 are integrally and externally fitted onto the two rear portions 34 and 35 of the flexible wiring substrate 30 (fold-shaping finished substrate), respectively. In this regard, the imaging module 10D is different from the imaging module 10 shown in FIG. 5B as an example.

By the resin 26 filling the inside of the tube and being cured, each insulating tube 28 is adhesively-fixed to and integrated with the front end of the built-in electrical cable 2 on which conductors are soldered on the flexible wiring substrate 30 (fold-shaping finished substrate) and the terminals of the rear portions 34 and 35.

The two rear portions 34 and 35 of the flexible wiring substrate 30 of the imaging module 10D include: the extended portions 34e and 35e which extend from both sides of the device-mounted portion 32 and are inclined with respect to the device-mounted portion 32 at an acute angle (sharp angle with respect to the mount back face 32b); and the connection end portions 34f and 35f extending from the extended portion 34e to the back side thereof, respectively.

However, in the configuration of the flexible wiring substrate 30 of the imaging module 10D, the connection end portions 34f and 35f of the two rear portions 34 and 35 are not directly connected to each other.

The flexible wiring substrate 30 of the imaging module 10D (fold-shaping finished substrate) is labeled as reference numeral 30A.

On the flexible wiring substrate 30A, the pair of rear portions 34 and 35 are adhesively-fixed to each other by use of the cured resin 39 filling the inside space enclosed in the device-mounted portion 32 and the extended portions 34e and 35e located at both sides of the device-mounted portion 32.

In the flexible wiring substrate 30A, the front edge configured by the device-mounted portion 32 and the extended portions 34e and 35e located at both sides of the device-mounted portion 32 is integrated into a body with the resin 39, and the shape stability of the front edge is ensured.

FIG. 16 shows a lens-attached imaging module 11A including a front-end imaging unit 12A having a structure in which the two insulating tubes 28 of the imaging module 10D accommodated in the metal frame member 41 are adhesively-fixed to and integrated with the metal frame member 41 by the cured resin 27 filling a gap between the metal frame member 41 and the insulating tube 28.

The two insulating tubes 28 of the imaging module 10D are adhesively-fixed to each other and integrated with each other by the resin 27 located inside the metal frame member 41.

Additionally, in the imaging module 10D, the positions at which the insulating tubes 28 are placed relative to the flexible wiring substrate 30 in the front-back direction are suitably variable as long as they are behind the extended portions 34e and 35e located at the front edge of the flexible wiring substrate 30A.

Moreover, as the insulating tube, a half-divided structure may be adopted instead of the insulating tube 28 that is a sleeve-shaped an integral molding. The half-divided structure is assembled in a cylindrical shape as a result of integrating tubes together with each other due to adhesive fixation by use of resin, thermal welding, or the like.

The preferred embodiments of the invention are described above, the invention is not limited to the aforementioned preferred embodiments, and various modifications may be made without departing from the scope of the invention.

For example, the flexible wiring substrate (fold-shaping finished substrate) of the imaging module related to the invention is not limited to a constitution in which each of extended portions extending from both sides of the device-mounted portion to the back side thereof is inclined with respect to the device-mounted portion at an acute angle.

As a flexible wiring substrate (fold-shaping finished substrate), a constitution can be adopted in which one of the two extended portions is only inclined with respect to the device-mounted portion at a sharp angle, the other of the extended portions substantially perpendicularly extends from the device-mounted portion to the rearward thereof, and the connection end portion extends from the rear edge of each extended portion backward.

Furthermore, in this case, a structure in which two connection end portions are arranged separately from each other can be adopted as well as a structure including extended tail portions having connection end portions connected to each other.

Here, in the case of the structure in which the two connection end portions are arranged separately from each other, a constitution is adopted in which, for example, a wiring and a terminal for connecting an electrical cable are provided on one or both opposed faces of two connection end portions facing each other, and the wiring is electrically connected to a wiring provided on a mount face side of the device-mounted portion via through-hole wiring or the like provided at the rear portion.

Additionally, the flexible wiring substrate (fold-shaping finished substrate) is not limited to a structure in which an connection end portion extends to the rearward from a rear edge of each extended portion extending from both sides of the device-mounted portion to the back side thereof, a structure can be adopted in which connection end portions are folded back from the back ends of the extended portions toward the device-mounted portion side and are positioned between two extended portions.

In this case, as the flexible wiring substrate, a constitution is adopted which includes a wiring and a terminal used to connect an electrical cable on the surface facing the extended portion to which each connection end portion is connected.

Moreover, for example, a cable-insertion hole is formed at a boundary between the extended portion and the connection end portion, and a conductor of a built-in electrical cable passing through the cable-insertion hole is soldered onto and electrically connected to the terminal of the connection end portion.

What is claimed is:

1. An imaging module comprising:
an electrical cable;
a solid-state image sensing device comprising an imaging unit orthogonal to a direction of an axis of a front end of the electrical cable; and
a flexible wiring substrate formed in an elongated shape in plan view, the flexible wiring substrate comprising:
a device-mounted portion onto which the solid-state image sensing device is mounted, the device-mounted portion having a mount back face;
a first portion that extends from a first side of the device-mounted portion in plan view showing the flexible wiring substrate, the first portion including a first extended portion and a first connection end portion;
a second portion that extends from a second side of the device-mounted portion in plan view showing the flexible wiring substrate, the second portion including a second extended portion and a second connection end portion, wherein
the first portion is connected to the second portion so that an internal space formed by the device-mounted portion, the first extended portion, and the second extended portion is filled with resin, at least a part of the first extended portion and the second extended portion is thereby fixed, and the first connection end portion is connected to the second connection end portion,
the first extended portion bends at the first side of the device-mounted portion and extends from the device-mounted portion,
the second extended portion bends at the second side of the device-mounted portion and extends from the device-mounted portion,
the first extended portion and the second extended portion extend so as to come close to each other with increasing distance from the device-mounted portion,
the first connection end portion extends from the first extended portion along the direction of the axis of the front end of the electrical cable on an opposite side of the device-mounted portion, the first connection end portion has a first opposed face, and the first opposed face is on the same face as the mount back face; and
the second connection end portion extends from the second extended portion along the direction of the axis of the front end of the electrical cable on an opposite side of the device-mounted portion, the second connection end portion has a second opposed face opposed to the first opposed face, and the second opposed face is on the same face as the mount back face,
wherein the first opposed face and the second opposed face are in contact with each other and the first connection end portion and the second connection end portion align in the direction of the axis of the front end of the electrical cable.

2. The imaging module according to claim 1, wherein the device-mounted portion, the first extended portion, the second extended portion, the first connection end portion, and the second connection end portion are provided only on one face of the flexible wiring substrate.

3. The imaging module according to claim 1, wherein the solid-state image sensing device comprises: a top face on which the imaging unit is provided; a back face electrically connected to the device-mounted portion of the flexible wiring substrate; wiring formed on the top face; and wiring formed on the back face, and
the wirings formed on the top face and on the back face are electrically connected through a through-hole interconnection which is formed and penetrated though the solid-state image sensing device.

4. The imaging module according to claim 1, wherein in a direction perpendicular to an extending direction of the first extended portion and the second extended portion, widths of the first extended portion and the second extended portion are smaller than widths of the first connection end portion and the second connection end portion extending from the first extended portion and the second extended portion, respectively.

5. The imaging module according to claim 1, wherein the flexible wiring substrate comprises bend portions that are located at the first side and the second side of the device-mounted portion of the flexible wiring substrate and protrude from a projection range of the solid-state image sensing device in the device-mounted portion.

6. The imaging module according to claim 5, wherein an insulation protection material does not coat the bend portion of the flexible wiring substrate so that wiring is exposed.

7. The imaging module according to claim 5, wherein a cut-off portion is formed at the bend portion of the flexible wiring substrate.

8. The imaging module according to claim 1, further comprising an insulating tube collectively accommodating the first connection end portion and the second connection end portion of the flexible wiring substrate and covering at least part of a connection portion between the flexible wiring substrate and the electrical cable.

9. The imaging module according to claim 1, further comprising an insulating tube externally fitted onto each of the first connection end portion and the second connection end portion of the flexible wiring substrate, covering at least part of a connection portion between the flexible wiring substrate and the electrical cable.

10. The imaging module according to claim 8, wherein the insulating tube is configured to include a half-divided structure in which a pair of tube divided bodies are connected to and integrated with each other.

11. The imaging module according to claim 9, wherein the insulating tube is configured to include a half-divided structure in which a pair of tube divided bodies are connected to and integrated with each other.

12. The imaging module according to claim 1, wherein the first connection end portion and the second connection end portion are fixed to each other, and
the flexible wiring substrate has a flexible portion located between a portion at which the first extended portion and the second extended portion are fixed and a portion at which the first connection end portion and the second connection end portion are fixed.

13. A lens-attached imaging module comprising a front-end imaging unit comprising: a flexible wiring substrate and a solid-state image sensing device which constitute the imaging module according to claim 1; a lens unit fixed to the solid-state image sensing device; and a sleeve-shaped metal frame member accommodating the flexible wiring substrate, the solid-state image sensing device, and the lens unit.

14. An endoscope comprising:
an insertion portion; and
the lens-attached imaging module according to claim 13, housed in the insertion portion.

* * * * *